(12) United States Patent
Jusuf et al.

(10) Patent No.: US 11,723,844 B2
(45) Date of Patent: Aug. 15, 2023

(54) NANOCERAMIC DENTAL PROSTHETIC

(71) Applicant: NATIONAL DENTEX, LLC, Palm Beach Gardens, FL (US)

(72) Inventors: Armand C. Jusuf, Reno, NV (US); Michael J. Mandeville, Reno, NV (US); Daniel R. Llop, Cornelius, NC (US)

(73) Assignee: NATIONAL DENTEX, LLC, Jupiter, FL (US)

( * ) Notice: Subject to any disclaimer, the term of this patent is extended or adjusted under 35 U.S.C. 154(b) by 518 days.

(21) Appl. No.: 16/804,519

(22) Filed: Feb. 28, 2020

(65) Prior Publication Data

US 2020/0306144 A1 Oct. 1, 2020

Related U.S. Application Data

(60) Provisional application No. 62/823,693, filed on Mar. 26, 2019.

(51) Int. Cl.
*A61C 1/08* (2006.01)
*A61K 6/802* (2020.01)
*A61C 8/00* (2006.01)
*A61C 13/225* (2006.01)

(52) U.S. Cl.
CPC .............. *A61K 6/802* (2020.01); *A61C 1/084* (2013.01); *A61C 8/0001* (2013.01); *A61C 8/0012* (2013.01); *A61C 8/0068* (2013.01); *A61C 8/0077* (2013.01); *A61C 13/225* (2013.01)

(58) Field of Classification Search
CPC ...... A61K 6/802; A61C 1/084; A61C 8/0001; A61C 8/0012; A61C 8/0068; A61C 8/0077; A61C 13/225
See application file for complete search history.

(56) References Cited

U.S. PATENT DOCUMENTS

| | | | |
|---|---|---|---|
| 8,899,984 B2 | 12/2014 | Llop et al. | |
| 9,504,533 B2 | 11/2016 | Groscurth et al. | |
| 9,693,834 B2 | 7/2017 | Llop | |
| 9,795,458 B2 | 10/2017 | Llop | |
| 2006/0014120 A1* | 1/2006 | Sapian | A61C 8/0057 433/169 |
| 2013/0071811 A1* | 3/2013 | Groscurth | A61C 8/0089 433/75 |
| 2014/0272778 A1 | 9/2014 | Llop | |

(Continued)

OTHER PUBLICATIONS

U.S. Appl. No. 62/781,054, entitled "Dental Bone Foundation Guide with Palatal or Fingual Side Gap and Freehand Surgical Guide," filed Dec. 18, 2018.

(Continued)

*Primary Examiner* — Nicholas D Lucchesi
(74) *Attorney, Agent, or Firm* — Frost Brown Todd LLP

(57) ABSTRACT

A method of installing a dental prosthetic device includes securing a first guide member to an alveolar arch in a mouth of a patient. The first guide member is utilized to achieve a substantially planar bone surface along the alveolar arch. A second guide member is coupled with the first guide member. The second guide member is utilized to install one or more implants in the alveolar arch through substantially planar bone surface. A dental prosthetic is secured to the one or more implants. The dental prosthetic includes nanoceramic material.

14 Claims, 17 Drawing Sheets

(56) References Cited

U.S. PATENT DOCUMENTS

| | | | |
|---|---|---|---|
| 2015/0010881 A1 | 1/2015 | Llop | |
| 2015/0272705 A1* | 10/2015 | Watson | A61C 8/0009 |
| | | | 433/199.1 |
| 2016/0038255 A1 | 2/2016 | Llop | |
| 2016/0278878 A1* | 9/2016 | Watson | A61C 13/01 |
| 2016/0338806 A1* | 11/2016 | Nazzal | A61C 13/0022 |
| 2017/0112591 A1 | 4/2017 | Llop | |
| 2017/0112592 A1 | 4/2017 | Groscurth et al. | |
| 2017/0252126 A1 | 9/2017 | Llop | |
| 2018/0110594 A1* | 4/2018 | Atkin | A61C 8/0027 |
| 2021/0137655 A1* | 5/2021 | Shen | C04B 41/5042 |
| 2021/0386529 A1* | 12/2021 | Tuckman | A61C 13/0018 |

OTHER PUBLICATIONS

U.S. Appl. No. 62/783,286, entitled "Dental Bone Foundation Guide with Bur Instrument Guide Features," filed Dec. 21, 2018.

U.S. Appl. No. 62/793,926, entitled "Dental Bone Foundation Guide with Reduced Bone Bevel Verification," filed Jan. 18, 2019.

\* cited by examiner

NANOCERAMIC DENTAL PROSTHETIC

PRIORITY

This application claims priority to U.S. Provisional Pat. App. No. 62/823,693, entitled "Nanoceramic Prosthetic," filed Mar. 26, 2019, the disclosure of which is incorporated by reference herein in its entirety.

BACKGROUND

Some patients may develop tooth loss warranting prosthetic replacement. Some instances may warrant a full dental arch restoration. To properly seat a permanent dental prosthetic, it may be necessary to remodel dental bone structures, thereby providing a substantially flat foundation for the prosthetic. After providing a substantially flat foundation, the dental clinician may drill passageways into the bone in which to secure implants. Once these passageways are formed and the implants are secured therein, the clinician may secure the prosthetic to the implants, thereby permanently affixing the prosthetic to the patient's bone.

Various forms of hardware may be used to perform the above-described surgical procedure. Examples of such hardware and associated procedures are described in U.S. Pat. No. 8,899,984, entitled "CT-Based, Side-Loading Surgical and Laboratory Dental Implant Guide System and Method," issued Dec. 2, 2014, the disclosure of which is incorporated by reference herein; U.S. Pat. No. 9,504,533, entitled "Endentulous Surgical Guide," issued Nov. 29, 2016, the disclosure of which is incorporated by reference herein; U.S. Pat. No. 9,693,834, entitled "Implant-Based Attachment System for Dental Implant Surgical Guide and Method," issued Jul. 4, 2017, the disclosure of which is incorporated by reference herein; U.S. Pat. No. 9,795,458, entitled "Dental Surgical Implant Guide and Prosthesis Combination and Method of Use," issued Oct. 24, 2017, the disclosure of which is incorporated by reference herein; U.S. Pub. No. 2014/0272778, entitled "Bone Foundation Guide and Method of Use," published Sep. 18, 2014, the disclosure of which is incorporated by reference herein; U.S. Pub. No. 2015/0010881, entitled "Bone Foundation Guide and Method of Use," published Jan. 8, 2015, the disclosure of which is incorporated by reference herein; U.S. Pub. No. 2016/0038255, entitled "Bone Foundation Guide System and Method," published Feb. 11, 2016, the disclosure of which is incorporated by reference herein; U.S. Pub. No. 2017/0112591, entitled "Bone Foundation Guide System and Method," published Apr. 27, 2017, the disclosure of which is incorporated by reference herein; U.S. Pub. No. 2017/0112592, entitled "Method of Using an Endentulous Surgical Guide," published Apr. 27, 2017, the disclosure of which is incorporated by reference herein; and U.S. Pub. No. 2017/0252126, entitled "Bone Foundation Guide System and Method," published Sep. 7, 2017, the disclosure of which is incorporated by reference herein.

While several dental surgical systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Exemplary Bone Foundation Guide

Figure 1:
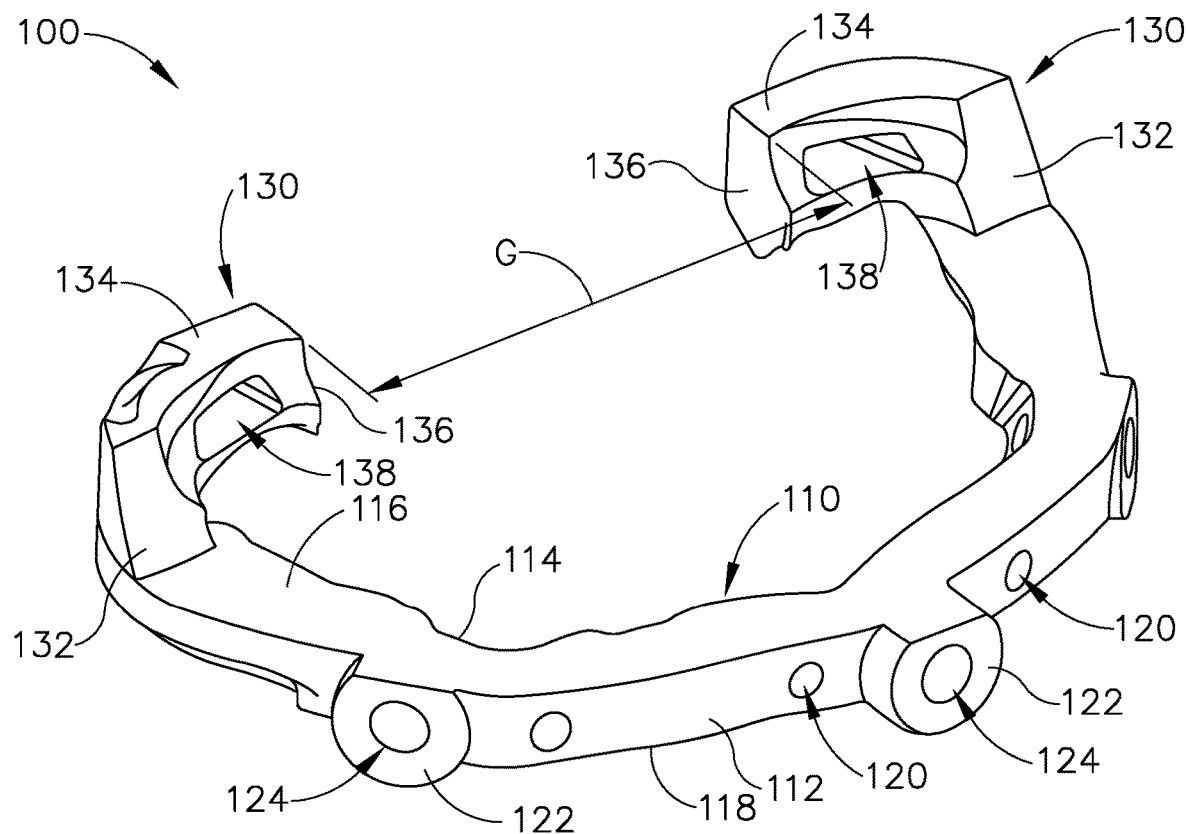
FIG. 1 depicts a perspective view of an exemplary bone foundation guide.
Figure 2:
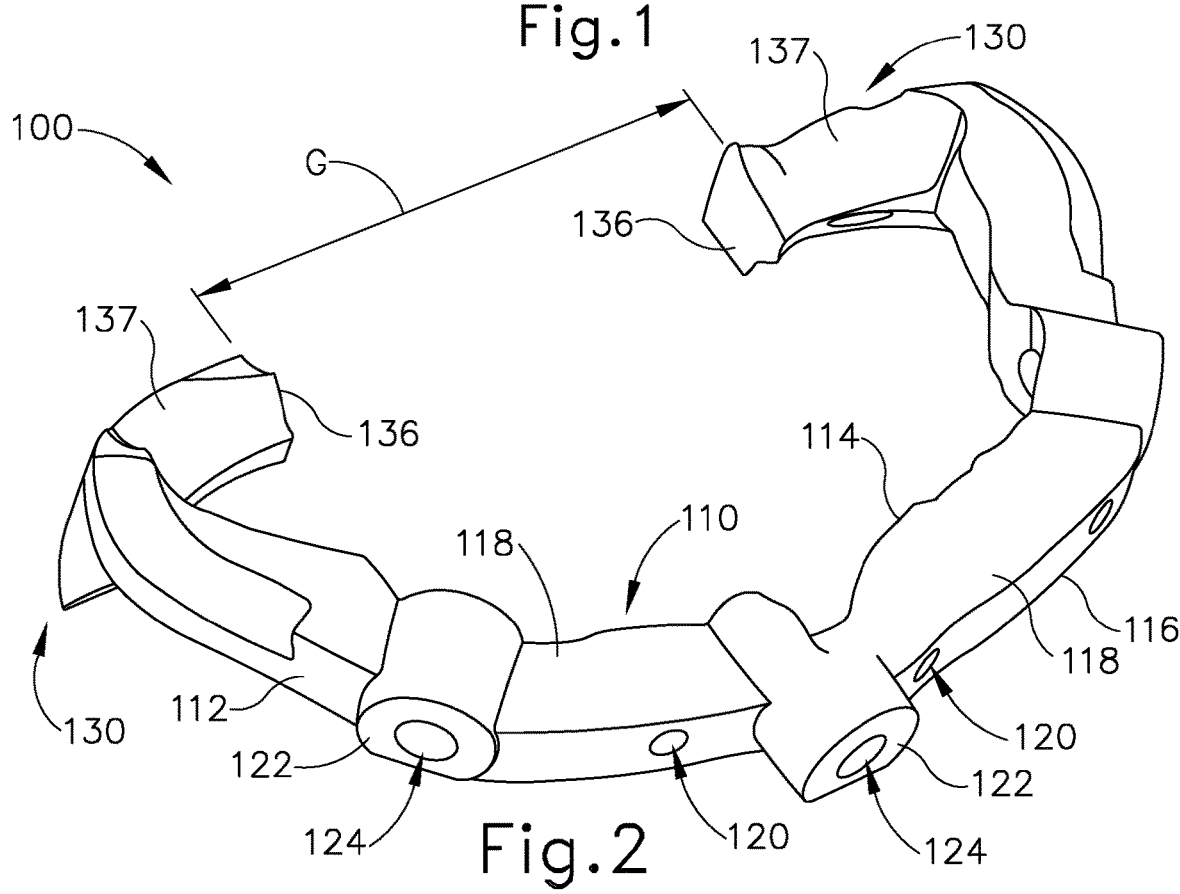
FIG. 2 depicts another perspective view of the bone foundation guide of FIG. 1.
Figure 3:
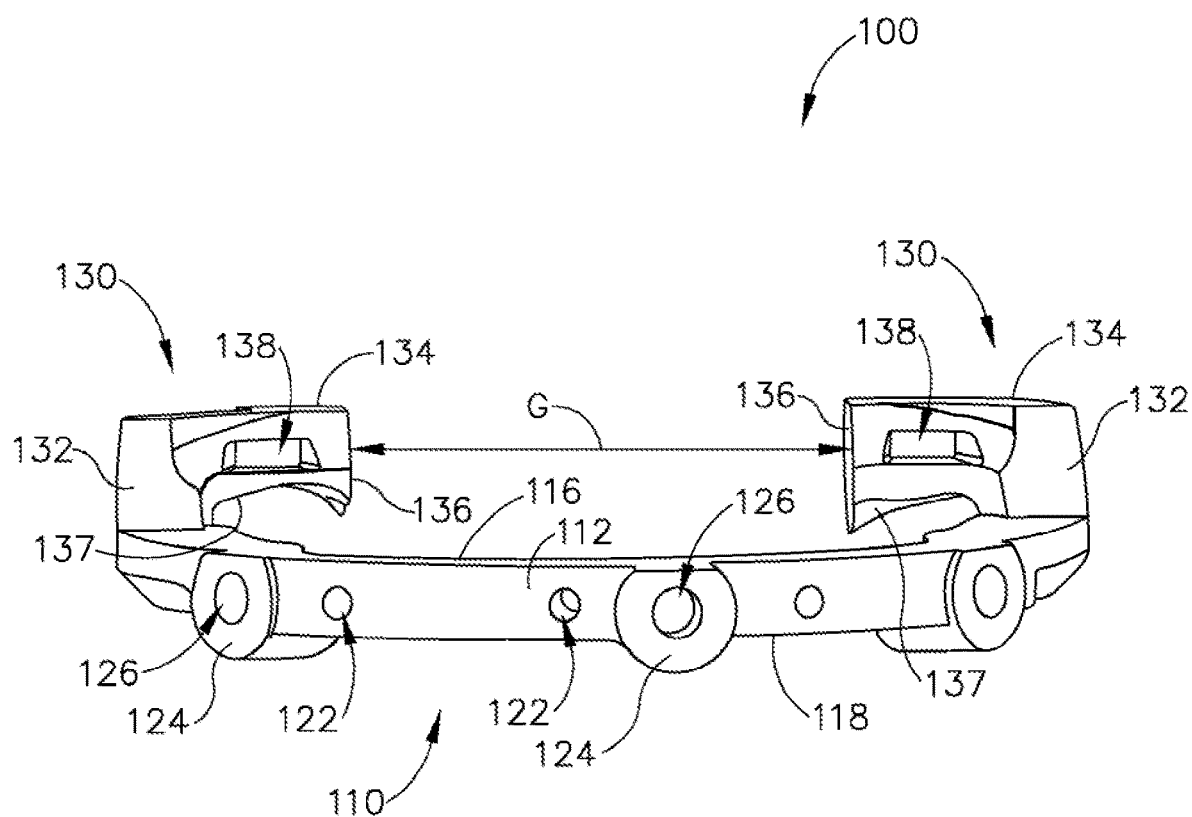
FIG. 3 depicts a front elevation view of the bone foundation guide of FIG. 1.
Figure 4:
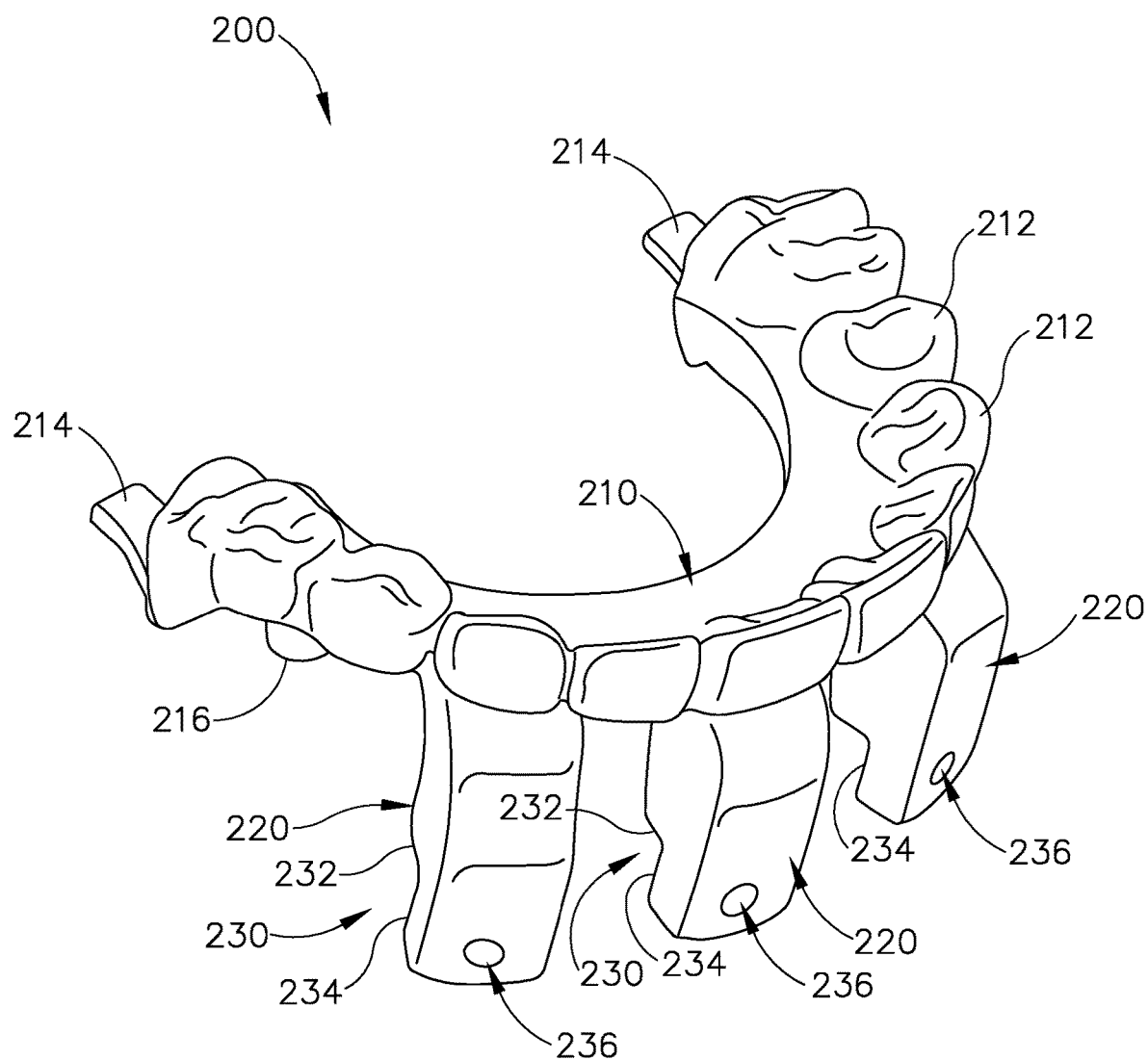
FIG. 4 depicts a perspective view of an exemplary strut assembly.

FIGS. 1-3 show an exemplary bone foundation guide (100), or bone reduction guide, that may be used in combination with other components in a surgical procedure as described below. Bone foundation guide (100) includes a horizontal body portion (110) and a pair of upright body portions (130). Horizontal body portion (110) extends along a horizontal plane and defines an arcuate shape corresponding to an alveolar arch of a patient, as described in greater detail below. Upright body portions (130) are located at each end of the arc defined by horizontal body portion (110). In some versions, bone foundation guide (100) is generated based on a three-dimensional digital model that is created based on a three-dimensional digital model of the patient's oral anatomy. Such a process may be performed in accordance with the teachings of any of the various patent references cited herein; and/or in accordance with the nSequence® Guided Prosthetics® Kit and workflow by National Dentex, LLC of Palm Beach Gardens, Fla.

Horizontal body portion (110) includes a front surface (112), a rear surface (114), an upper surface (116), and a lower surface (118). The terms "upper" and "lower" are being used herein in the exemplary context of bone foundation guide (100) and other devices being mounted to the mandibular alveolar arch. However, as noted below, some versions of bone foundation guide (100) may be mounted to the maxillary alveolar arch, in which cases upper surface (116) would in fact be presented downwardly; and lower source (118) upwardly. Use of the terms "upper" and "lower" should therefore not be read as limiting the alveolar ridge to which bone foundation guide (100) may be secured.

In the present example, rear surface (114) is configured to correspond directly to the configuration of the front-facing surface of the patient's alveolar arch, to thereby provide full surface-to-surface contact along the entirety of rear surface (114) when bone foundation guide (100) is fully seated on the alveolar arch. Rear surface (114) is thus configured to closely mate with a corresponding region of the bone structure of the alveolar arch of the patient. The configuration of rear surface (114) is customized per patient in this example, such that the configuration of rear surface (114) is based upon the anatomical surface geometry embodied in the three-dimensional digital model of the patient's anatomy. Upper surface (116) is substantially flat in this example, to thereby provide a substantially horizontal plane for guidance of a bone reduction procedure as described below.

Horizontal body portion (110) also includes a plurality of passageways (120, 124) extending from front surface (112) to rear surface (114). Passageways (120) are configured to align with corresponding passageways (236, 324) of a strut assembly (200) and a surgical guide (300) as will be described in greater detail below. Passageways (124) are configured to receive fasteners to secure bone foundation guide (100) to the alveolar ridge of a patient. By way of example only, bone foundation guide (100) may be secured to the alveolar ridge via pins, screws, or other features disposed in passageways (124). Passageways (124) are surrounded by cylindraceous stand-off features (122) in the present example. Stand-off features (122) are configured to reinforce the structural integrity of horizontal body portion (110) in the regions around passageways (124).

Each upright body portion (130) includes a vertically extending front surface (132), a horizontally extending upper surface (134), a vertically extending inner surface (136), and a lower surface (137). A slot (138) is formed through each upright body portion (130). In the present example, surfaces (132, 134, 136) are generally flat. A gap (G) extends laterally between inner surfaces (136). Lower surface (137) is configured to correspond directly to the configuration of an upwardly facing surface of the patient's alveolar arch (or the downwardly facing surface when bone foundation guide (100) is mounted to the maxillary alveolar arch), to thereby provide full surface-to-surface contact along the entirety of lower surface (137) when bone foundation guide (100) is fully seated on the alveolar arch. Lower surface (137) is thus configured to closely mate with the bone structure of a corresponding region of the alveolar ridge of the patient. The configuration of lower surface (137) is customized per patient in this example, such that the configuration of lower surface (137) is based upon the anatomical surface geometry embodied in the three-dimensional digital model of the patient's anatomy.

As best seen in FIG. 3, each lower surface (137) is positioned vertically higher than the horizontal plane of upper surface (116) in this example. Similarly, slots (138) are also positioned vertically higher than the horizontal plane of upper surface (116) in this example.

Those skilled in the art will recognize that bone foundation guide (100) of this example has only one single horizontal body portion (110) in this example. The single horizontal body portion (110) is configured to fit only on the buccal side of a patient's alveolar arch in this example—regardless of whether it is the mandibular alveolar arch or the maxillary alveolar arch—as will be described in greater detail below. Unlike conventional bone foundation guides, there is no additional horizontal body portion (110) that fits on the palatal or lingual side of the alveolar arch. This may provide in a reduced cost to manufacture bone foundation guide (100) due to the reduction of materials. Omitting a horizontal body portion (110) that fits on the palatal or lingual side of the alveolar arch may also reduce the amount of gum (G) tissue that needs to be moved away from bone (B) during installation of bone foundation guide (100) on the alveolar arch. The omission of a horizontal body portion (110) that fits on the palatal or lingual side of the alveolar arch may also improve the accuracy of seating of bone foundation guide (100) on the alveolar arch because the palatal or lingual tissue does not interfere with or otherwise contact horizontal body portion. In addition, the absence of a horizontal body portion (110) that fits on the palatal or lingual side of the alveolar arch may also improve visualization of anatomical structures such as arteries attached to gingiva, etc. The omission of a horizontal body portion (110) that fits on the palatal or lingual side of the alveolar arch may also assist in keeping the implant sites irrigated and cool. Other potential advantages of the configuration of bone foundation guide (100) of the present example will be apparent to those skilled in the art in view of the teachings herein.

By way of example only, bone foundation guide (100) may be formed using rapid prototyping equipment (e.g., 3D printing or other additive manufacturing, etc.), based on a three-dimensional digital model as noted above. By way of further example only, bone foundation guide (100) may be formed of plastic, metal, other materials, and combinations thereof. For instance, some versions of bone foundation guide (100) may be formed of 3D printed steel. Various suitable ways in which bone foundation guide (100) may be formed will be apparent to those skilled in the art in view of the teachings herein.

II. Exemplary Strut Assembly

FIGS. 4-8 show an exemplary strut assembly (200) that may be used in combination with bone foundation guide (100) in a surgical procedure as described below. Strut assembly (200) includes a horizontal body portion (210) and a set of strut members (220). Horizontal body portion (210) extends along a horizontal plane and defines an arcuate shape corresponding to an alveolar arch of a patient, as described in greater detail below. A set of three-dimensional representations of prosthetic teeth (212) project upwardly from horizontal body portion (210). These teeth (212) correspond to the teeth of a full dental arch prosthetic device that will ultimately be installed on the patient's alveolar arch. Thus, the surface geometry of teeth (212) may be identical to the surface geometry of the teeth on the prosthetic device; with both being generated in a three-dimensional digital model using known techniques.

A pair of tabs (214) extend proximally from each free end of the arc formed by horizontal body portion (210). Tabs (214) provide structures for coupling strut assembly (200) with bone foundation guide (100) as described in greater detail below. The underside of body portion (210) includes a set of downwardly projecting studs (216). Studs (216) of the present example serve as anatomical bone positioning stops and are configured to engage anatomical structures of the alveolar ridge when the combination of strut assembly (200) and bone foundation guide (100) are mounted to the alveolar ridge, as described in greater detail below. In some variations, studs (216) are omitted.

Figure 5:
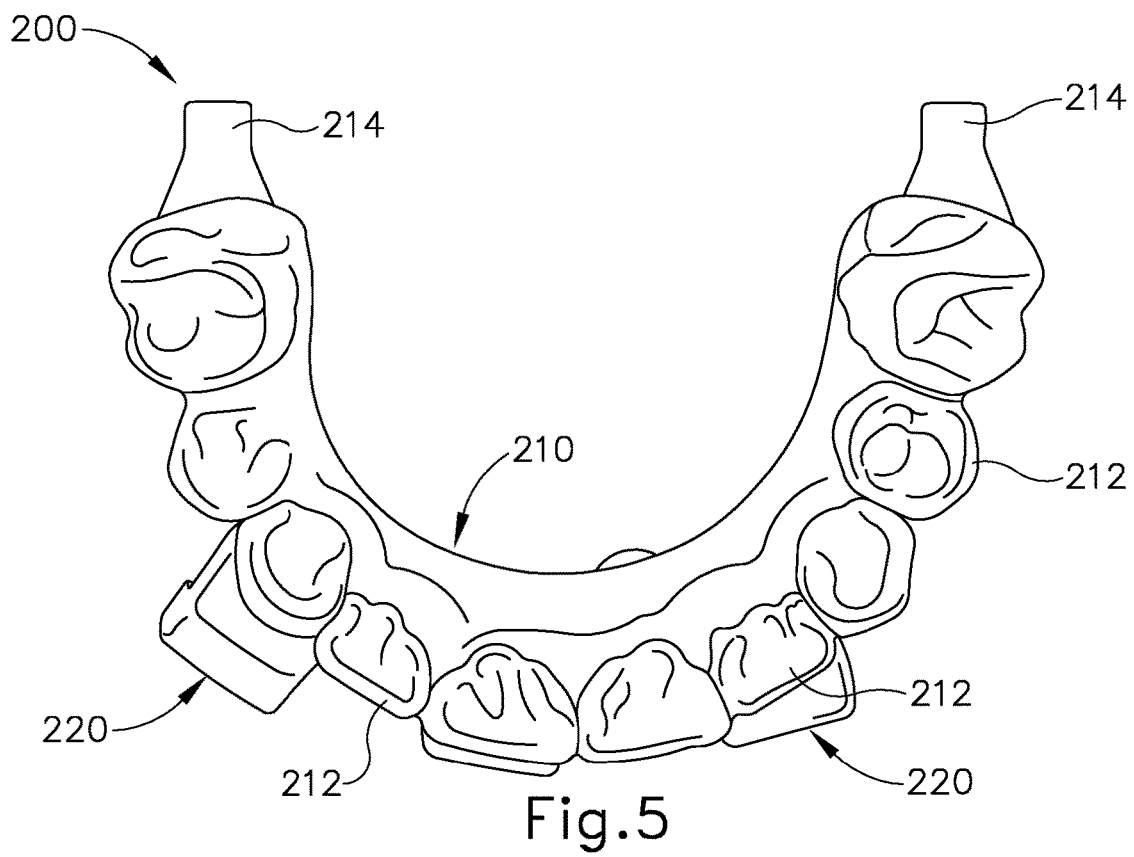
FIG. 5 depicts a top plan view of the strut assembly of FIG. 4.
Figure 6:
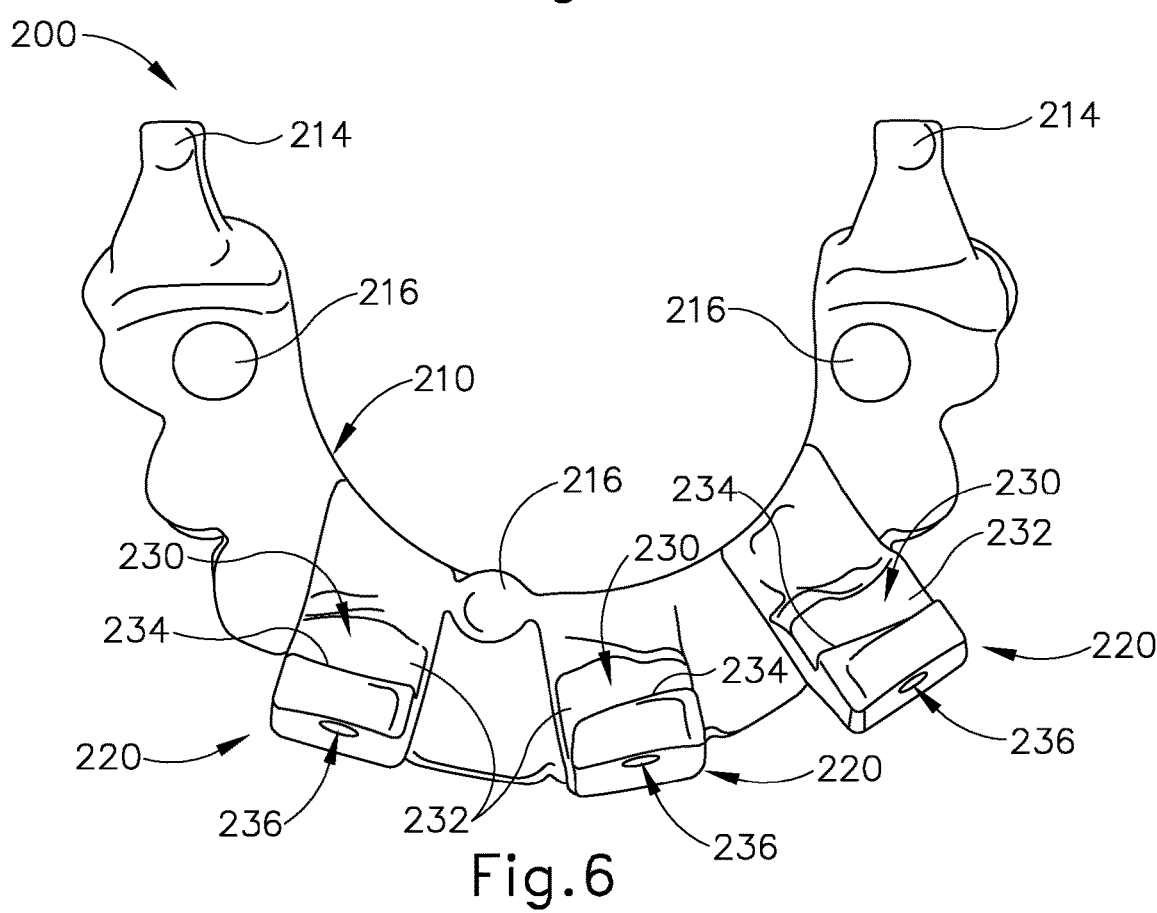
FIG. 6 depicts a bottom plan view of the strut assembly of FIG. 4.
Figure 7:
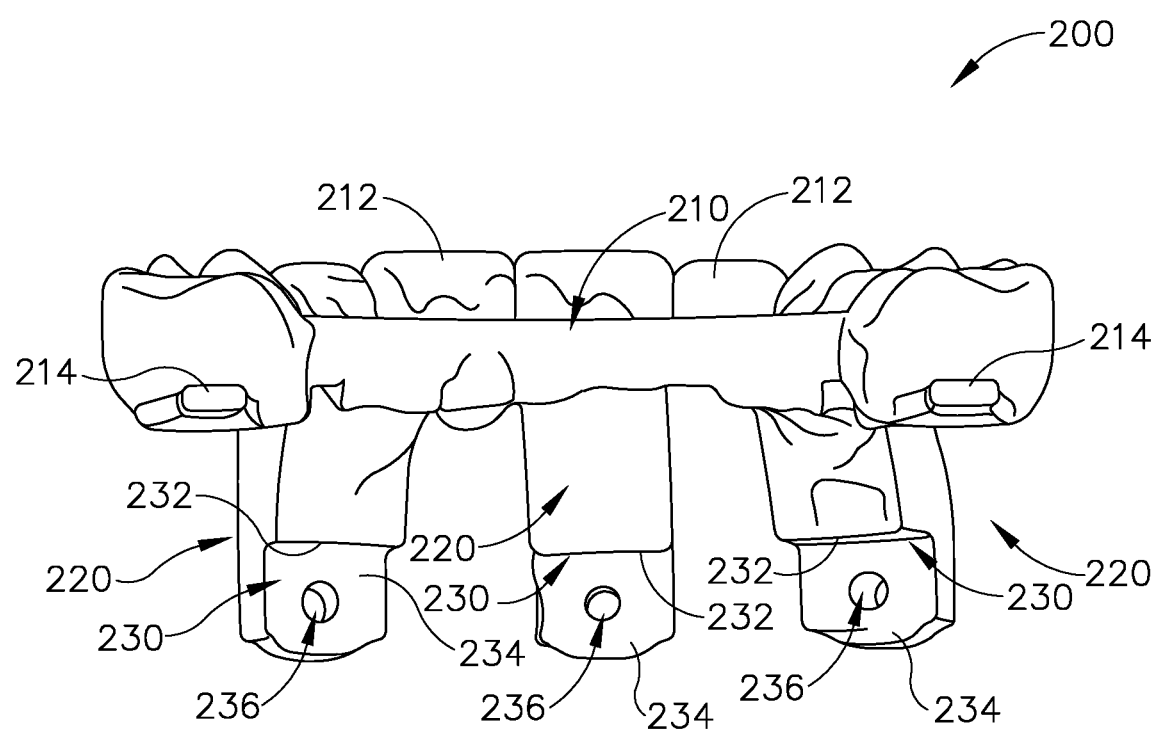
FIG. 7 depicts a rear elevation view of the strut assembly of FIG. 4.
Figure 8:
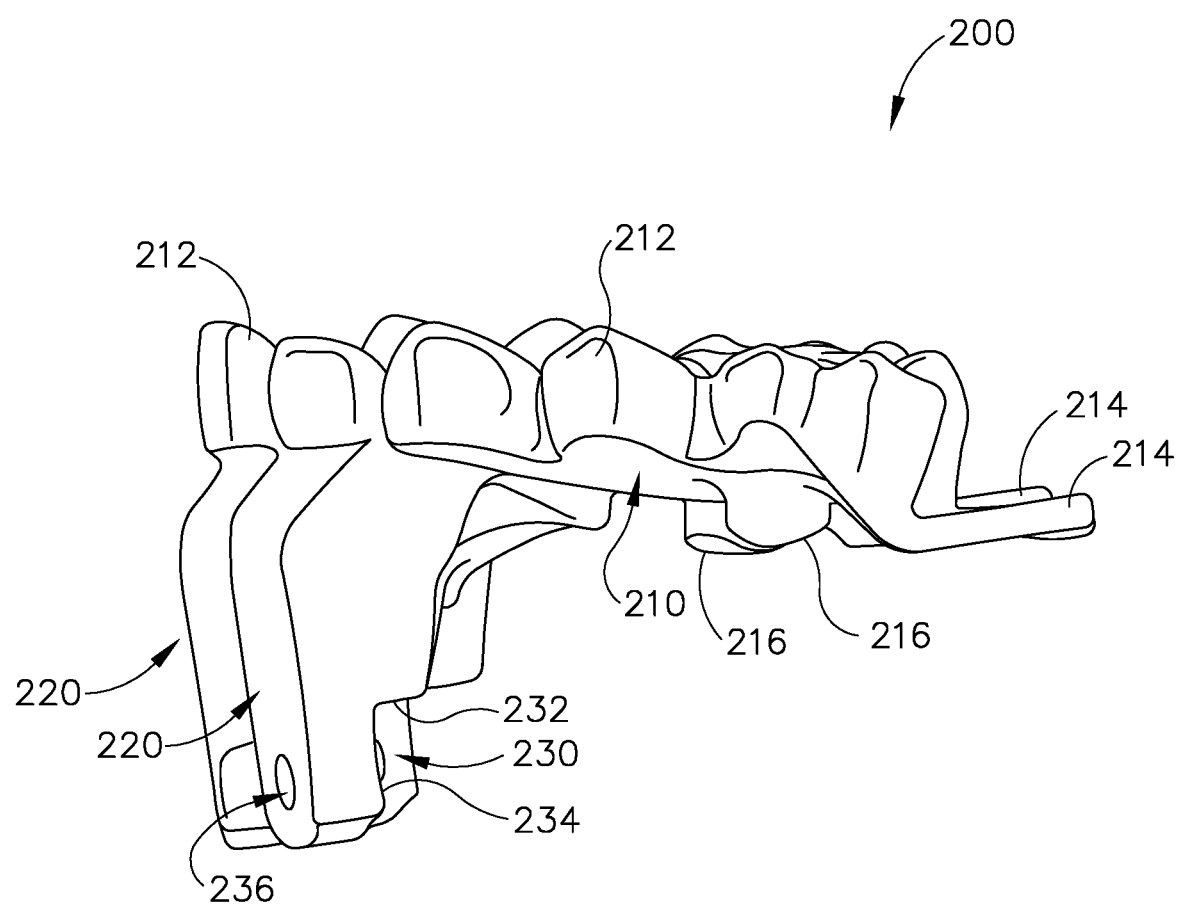
FIG. 8 depicts a side elevation view of the strut assembly of FIG. 4.

Strut assembly (200) includes three strut members (220) in the present example, though strut assembly (200) may instead include more or fewer than three strut members (220). Each strut member (220) includes a passageway (236) and a shelf portion (230). Each shelf portion (230) includes a downwardly facing surface (232) and a rear facing surface (234). Surfaces (232, 234) together form a right angle in this example. As best seen in FIG. 5, portions of one or more strut members (220) may project distally past the arc of teeth (212).

By way of example only, strut assembly (200) may be formed using rapid prototyping equipment (e.g., 3D printing or other additive manufacturing, etc.), based on a three-dimensional digital model as noted above. By way of further example only, strut assembly (200) may be formed of plastic, metal, other materials, and combinations thereof. Various suitable ways in which strut assembly (200) may be formed will be apparent to those skilled in the art in view of the teachings herein.

Figure 9:
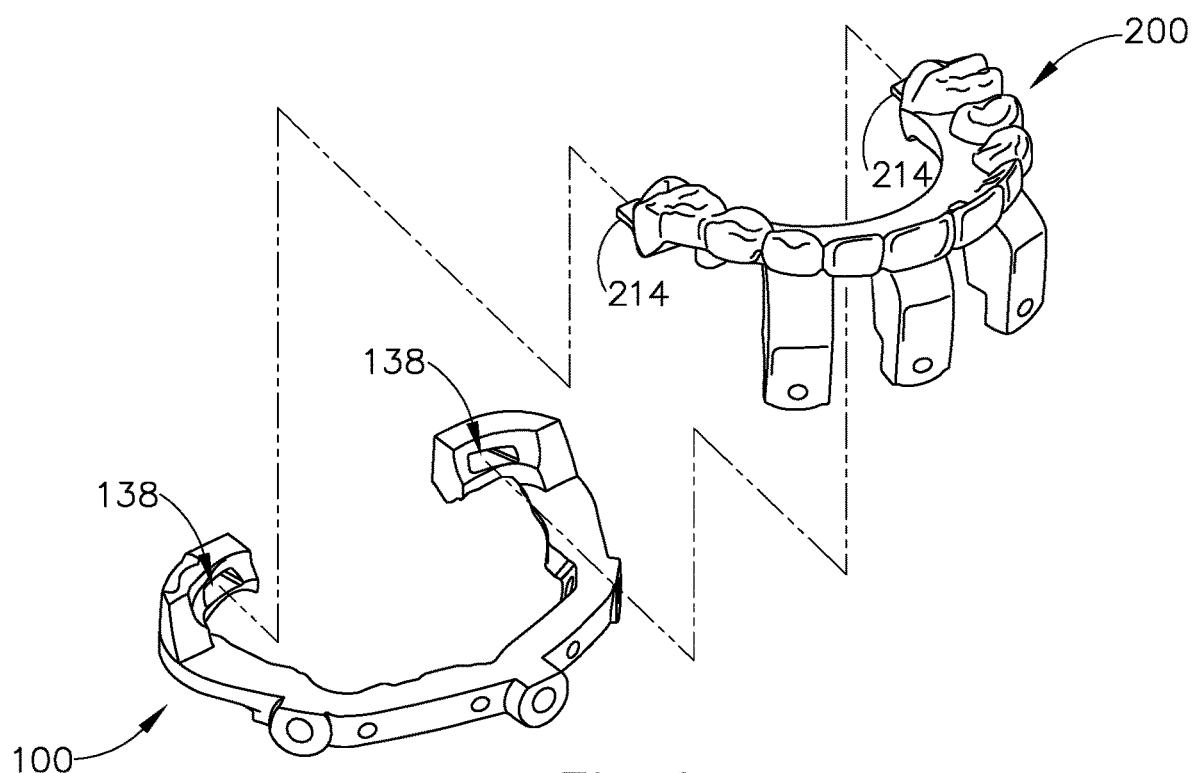
FIG. 9 depicts an exploded perspective view of a combination of the bone foundation guide of FIG. 1 and the strut assembly of FIG. 4.
Figure 10:
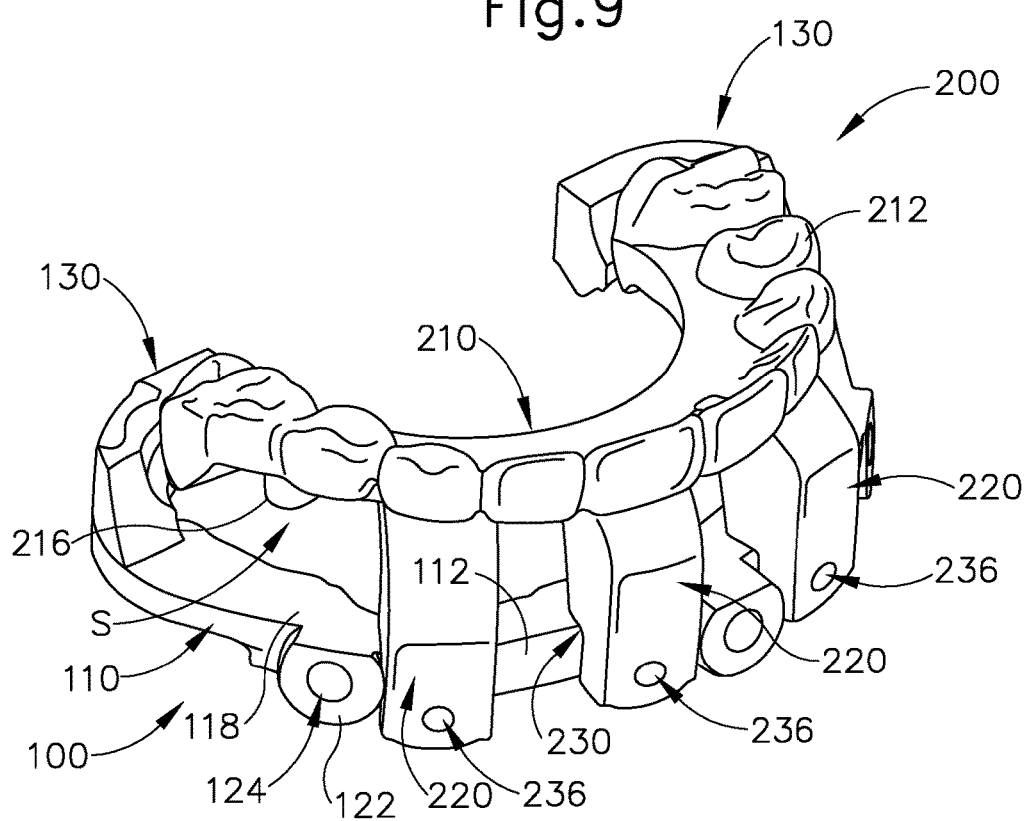
FIG. 10 depicts a perspective view of the strut assembly of FIG. 4 assembled with the bone foundation guide of FIG. 1.
Figure 11:
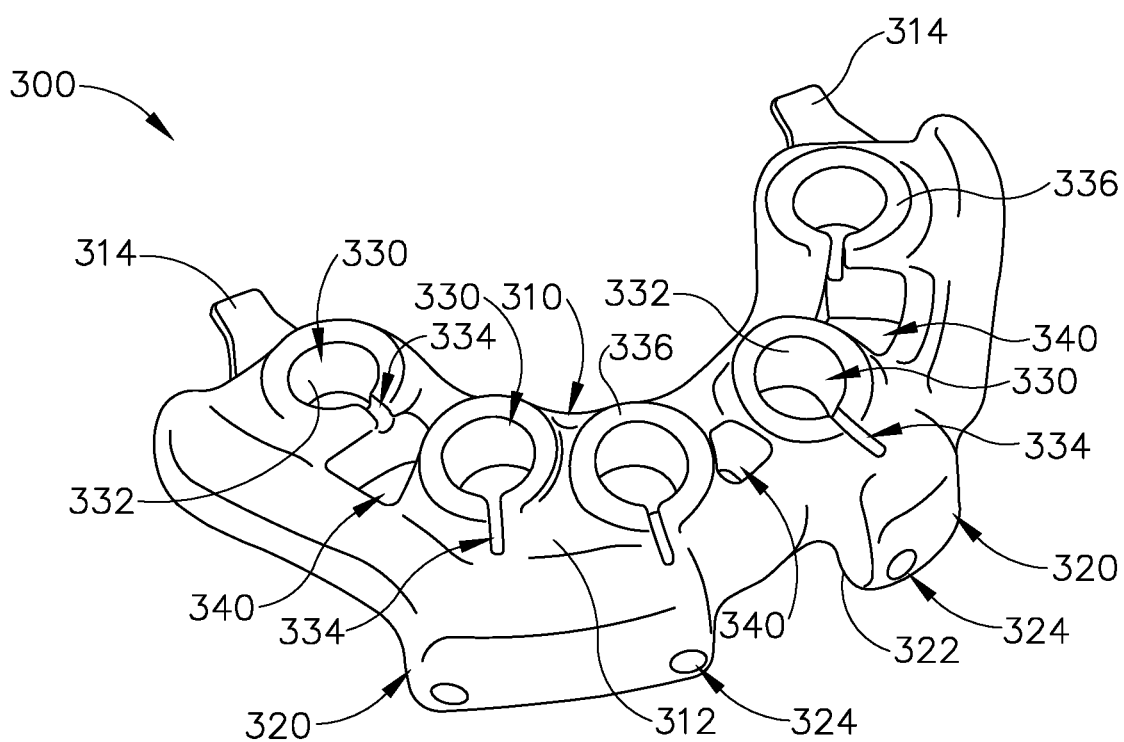
FIG. 11 depicts a perspective view of an exemplary surgical guide.
Figure 12:
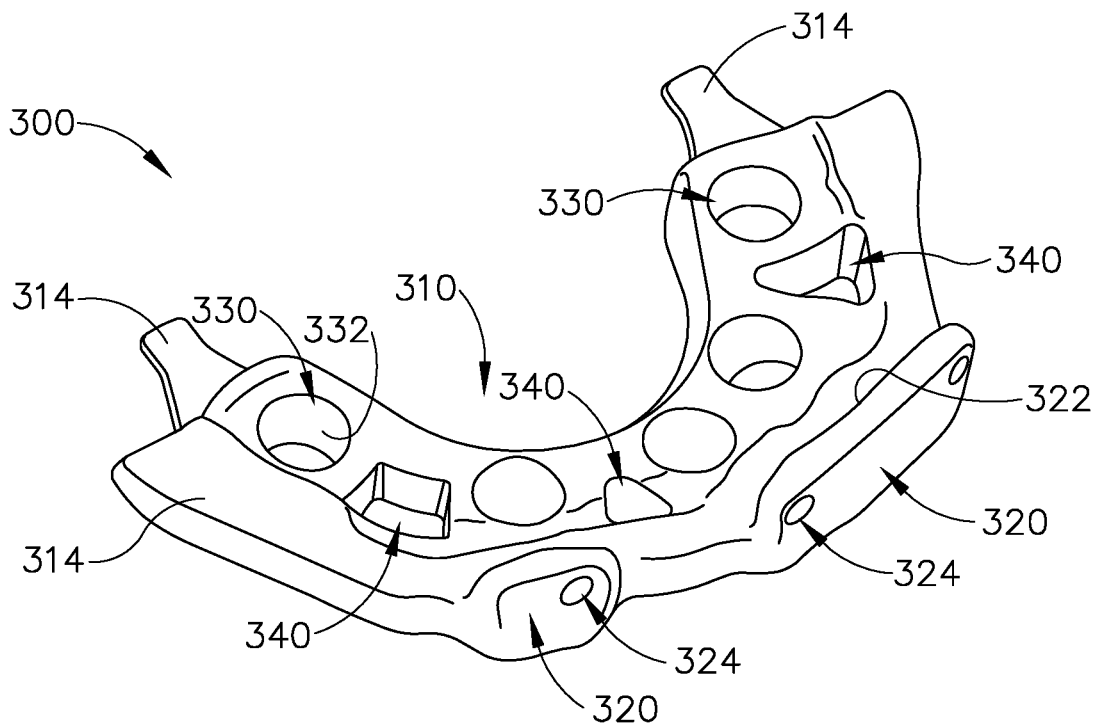
FIG. 12 depicts another perspective view of the surgical guide of FIG. 11.
Figure 13:
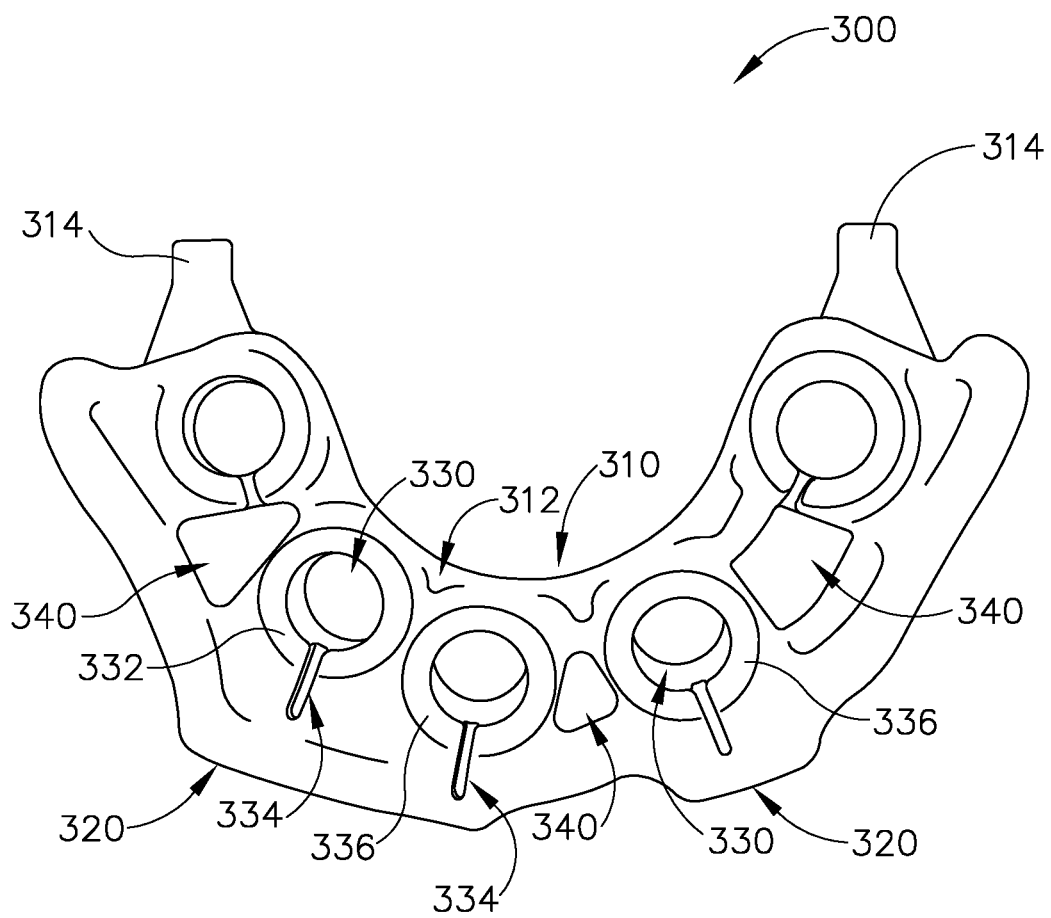
FIG. 13 depicts a top plan view of the surgical guide of FIG. 11.
Figure 14:
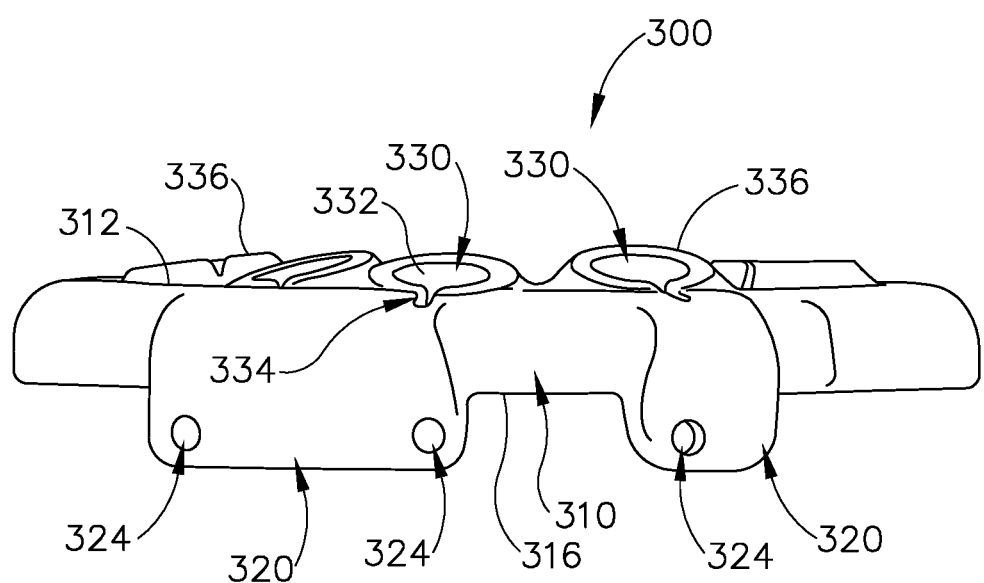
FIG. 14 depicts a front elevation view of the surgical guide of FIG. 11.
Figure 15:
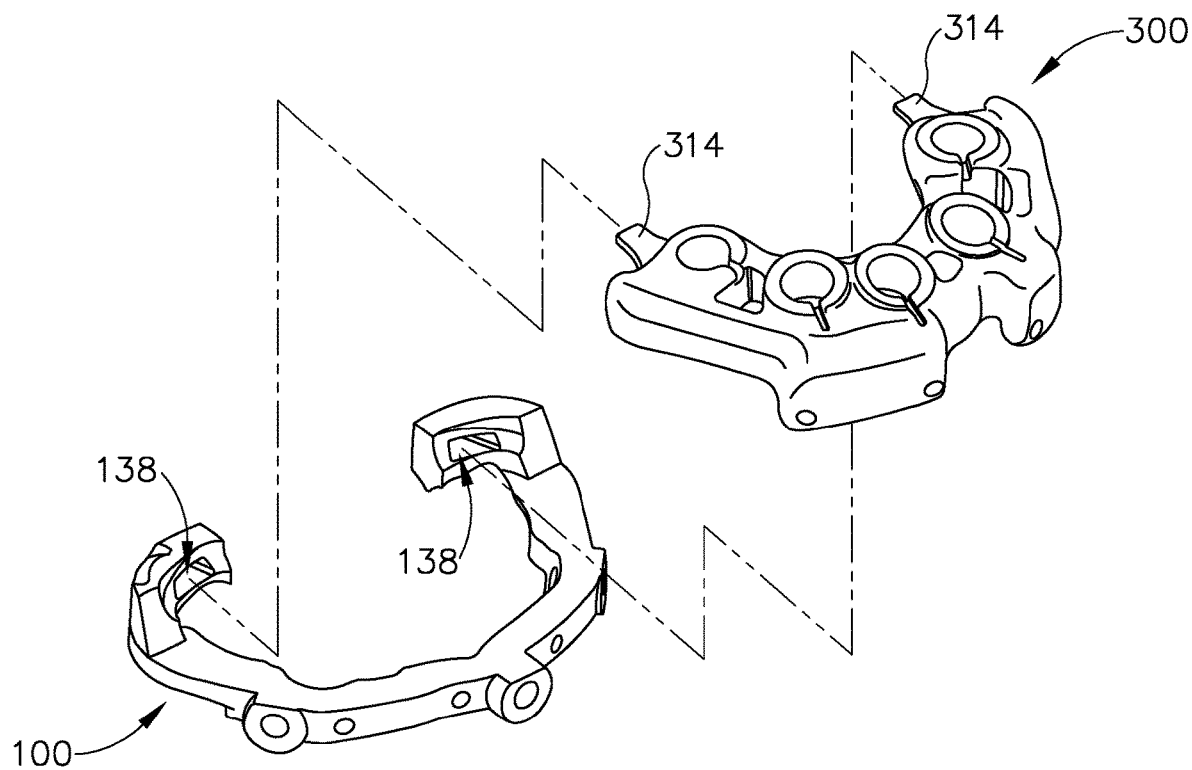
FIG. 15 depicts an exploded perspective view of a combination of the bone foundation guide of FIG. 1 and the surgical guide of FIG. 11.
Figure 16:
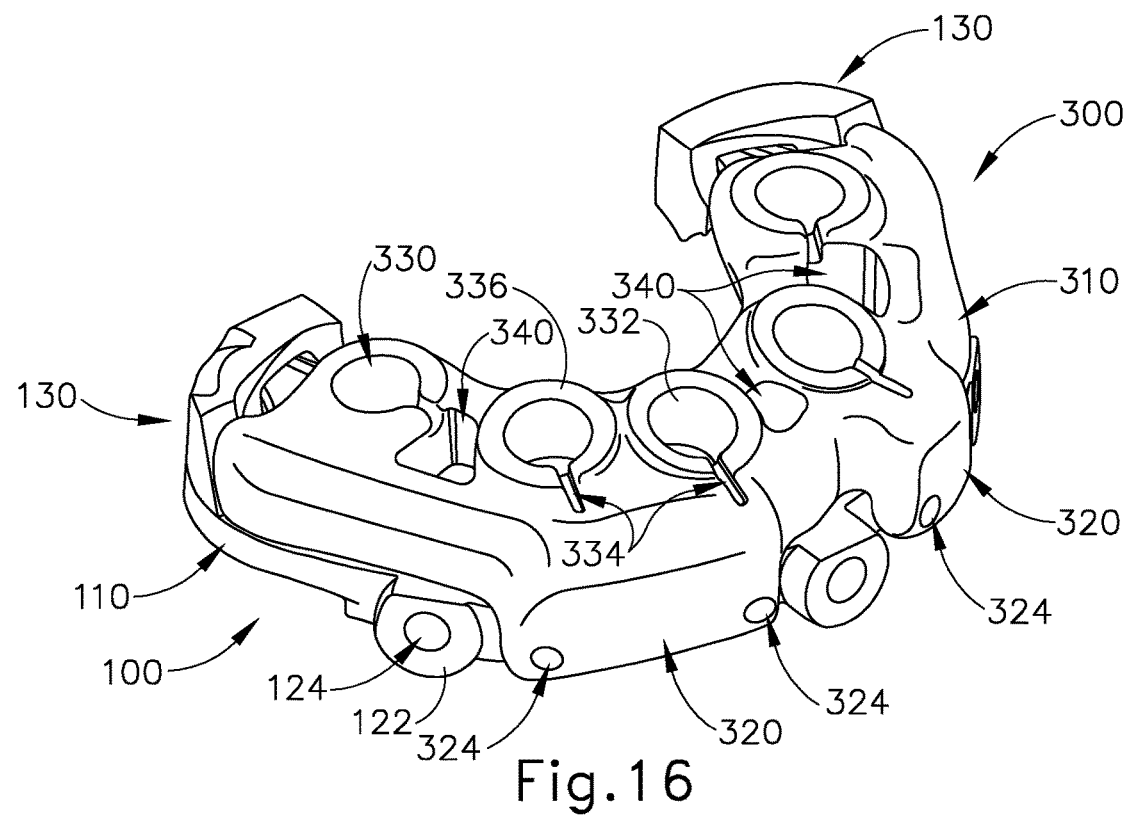
FIG. 16 depicts a perspective view of the surgical guide of FIG. 11 assembled with the bone foundation guide of FIG. 1.
Figure 17:
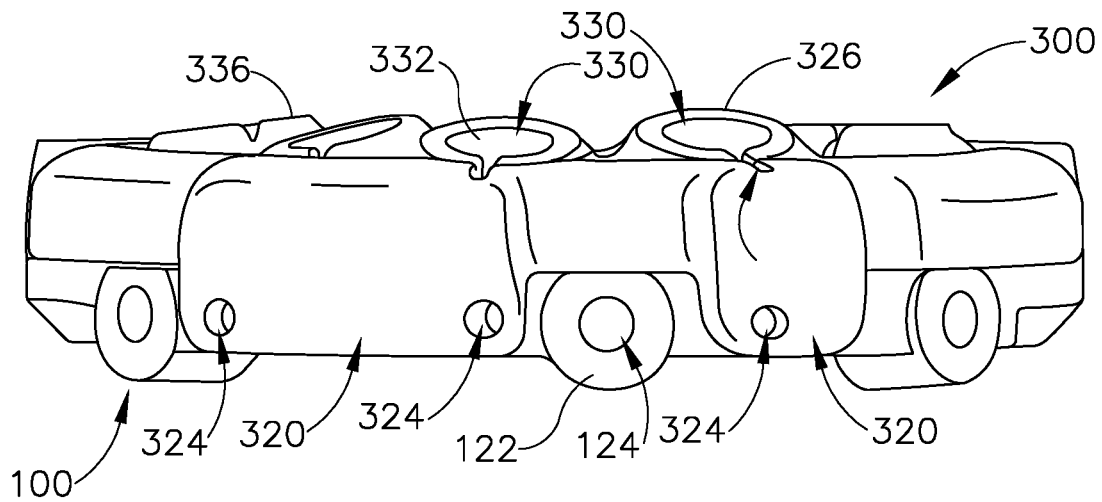
FIG. 17 depicts a front elevation view of the surgical guide of FIG. 11 assembled with the bone foundation guide of FIG. 1.
Figure 18:
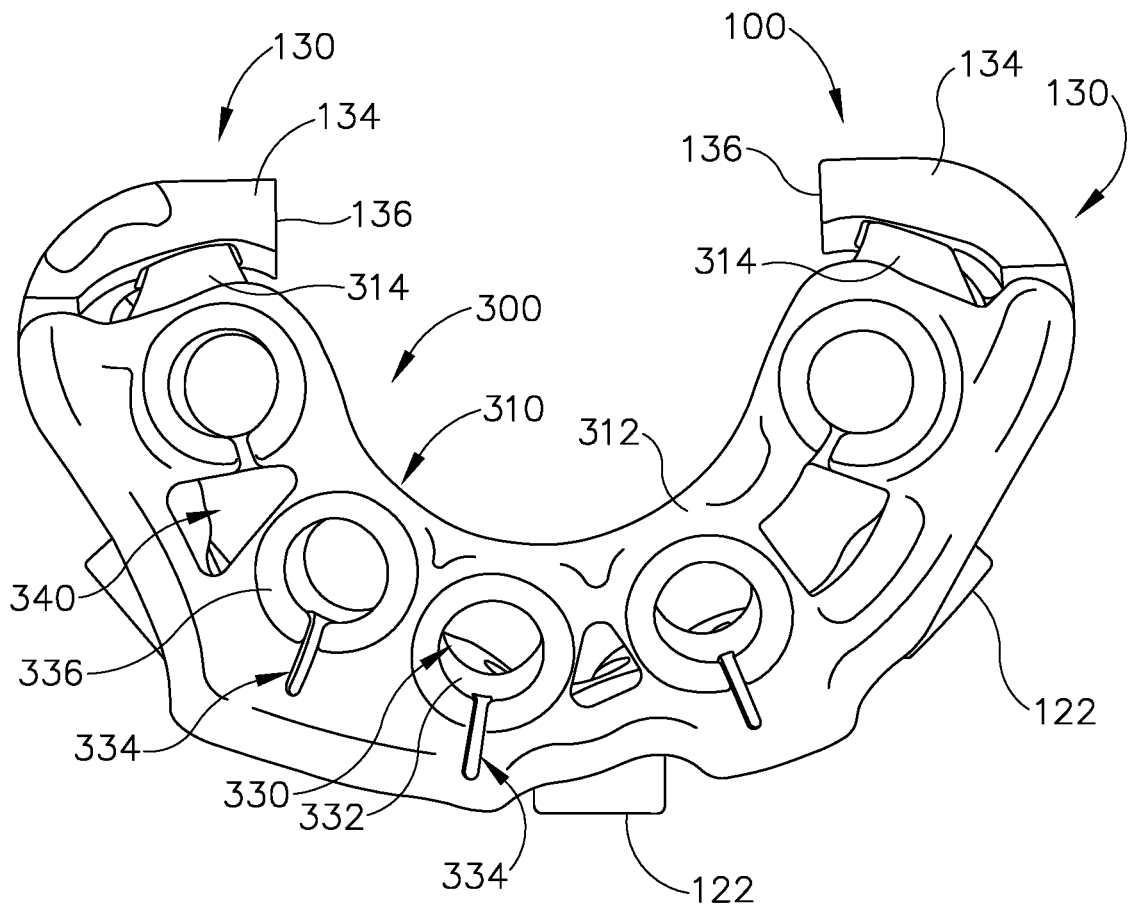
FIG. 18 depicts a top plan view the surgical guide of FIG. 11 assembled with the bone foundation guide of FIG. 1.

FIGS. 9-10 show how strut assembly (200) and bone foundation guide (100) may be coupled together. As shown, tabs (214) of strut assembly (200) may be inserted into corresponding slots (138) of bone foundation guide (100). Strut members (220) of strut assembly (200) are configured to engage horizontal body portion (110) of bone foundation guide (100). When strut members (220) are engaged with horizontal body portion (110), shelf portions (230) of strut members (220) receive horizontal body portion (110). Thus, each downwardly facing surface (232) of each strut member (220) engages upper surface (118) of horizontal body portion (110); and each rear facing surface (232) of each strut member (220) engages front surface (112) of horizontal body portion (110). Passageways (236) of strut members (220) are aligned with passageways (122) of horizontal body potion (110) when strut assembly (200) is coupled with bone foundation guide (110). The height of strut members (220) puts teeth (210) in position for normal occlusal engagement with the teeth of the other alveolar ridge of the patient, as will be described in greater detail below.

III. Exemplary Surgical Guide

FIGS. 11-14 show an exemplary surgical guide (300) that may be used in combination with bone foundation guide (100) in a surgical procedure as described below. Surgical guide (300) includes a horizontal body portion (310) and a set of flange members (320). Horizontal body portion (310) extends along a horizontal plane and defines an arcuate shape corresponding to an alveolar arch of a patient, as described in greater detail below. A set of guide passageways (330) extend through horizontal body portion (310). Each guide passageway (330) includes a cylindraceous inner surface (332), a flat top surface (336), and a guide notch (334).

Inner surfaces (332) are oriented to guide a conventional drilling instrument along the appropriate path to drill openings to receive implants as will be described in greater detail below. Inner surfaces (332) may also assist in guiding instrumentation used to install the implants in the openings after the openings are drilled in the alveolar arch. Moreover, inner surfaces (332) may assist in guiding instrumentation used to install abutments on the implants after the implants are installed in the alveolar arch. In some instances, one or more inner surfaces (332) may be vertically oriented, such that inner surfaces (332) are perpendicular to the horizontal plane associated with horizontal body portion (310). In other instances, one or more inner surfaces (332) may be obliquely oriented relative to the horizontal plane associated with horizontal body portion (310). In the present example, each top surface (336) is perpendicular to the adjacent inner surface (332), regardless of whether inner surface (332) is perpendicular or oblique relative to the horizontal plane associated with horizontal body portion (310). Top surfaces (336) are configured to provide a hard stop for master tube insertion into the corresponding guide passageways (330), thereby controlling the depth of implants that are inserted into bone (B) via passageways (330). In other words, top surfaces (336) may engage corresponding implant mount flanges to thereby arrest insertion of implants via passageways (330) at corresponding predetermined depths of insertion.

Each guide notch (334) is positioned at a prescribed angular orientation about the longitudinal axis of the corresponding guide passageway (330). The angular orientations of guide notches (334) may vary from patient to patient; and the angular orientations of guide notches (334) may vary from guide passageway (330) to guide passageway (330) within the same surgical guide (300). Each guide notch (334) is configured and oriented to provide the clinician with a visual cue as to where to angularly align a corresponding notch of an implant mount that is inserted via the corresponding guide passageway (330). This may ensure accurate rotation of the dental implant and corresponding dental implant abutment to line up properly with the predetermined exit hole in the top of a dental prosthesis that will ultimately be secured to the dental implant abutments.

A pair of tabs (314) extend proximally from each free end of the arc formed by horizontal body portion (310). Tabs (314) provide structures for coupling surgical guide (300) with bone foundation guide (100) as described in greater detail below. Horizontal body portion (310) also includes a set of openings (340) extending vertically through horizontal body portion (310), from a top surface (312) of horizontal body portion (310) to a bottom surface (316) of horizontal body portion (310). Openings (340) may assist in providing windows for visualization of bone (B) underneath surgical guide (300), as well as visualization of dental drills and implants inserted through guide passageways (330). Openings (340) may also provide additional pathways for irrigation fluid (e.g., water, saline, etc.) to reach bone (B) underneath surgical guide (300).

Surgical guide (300) includes two flange members (320) in this example, though surgical guide (300) may instead include more or fewer than two flange members (320). One flange member (320) includes two passageways (324) while the other flange member (320) includes only one passageway (324) in this example. Each flange member (320) includes a rear facing surface (322). Flange members (320) are positioned along the distal or buccal side of body portion (310) and are thereby positioned to engage front surface (112) of bone foundation guide (100) as will be described in greater detail below.

By way of example only, surgical guide (300) may be formed using rapid prototyping equipment (e.g., 3D printing or other additive manufacturing, etc.), based on a three-dimensional digital model as noted above. By way of further example only, surgical guide (300) may be formed of plastic, metal, other materials, and combinations thereof. In some versions, the majority of surgical guide (300) is formed of plastic, while guide passageways (330) are lined with metallic cylinders. Various suitable ways in which surgical guide (300) may be formed will be apparent to those skilled in the art in view of the teachings herein.

FIGS. 15-18 show how surgical guide (300) and bone foundation guide (100) may be coupled together. As shown, tabs (314) of surgical guide (300) may be inserted into corresponding slots (138) of bone foundation guide (100). Bottom surface (316) of horizontal body portion (310) of surgical guide (300) rests atop upper surface (116) of horizontal body portion (110) of bone foundation guide (100). Each rear facing surface (322) of each flange member (320) engages front surface (112) of horizontal body portion (110). Passageways (324) of flange members (320) are aligned with passageways (122) of horizontal body potion (110) when surgical guide (300) is coupled with bone foundation guide (110). When surgical guide (300) and bone foundation guide (100) are coupled together, passageways (330) are positioned and aligned to structurally guide the drilling of openings for implants and the installation of implants in the drilled openings, as will be described in greater detail below.

As another merely illustrative alternative, surgical guide (300) may be replaced with a freehand surgical guide that is constructed and operable in accordance with at least some of the teachings of U.S. Provisional Pat. App. No. 62/781,054, entitled "Dental Bone Foundation Guide with Palatal or Lingual Side Gap and Freehand Surgical Guide," filed Dec. 18, 2018, the disclosure of which is incorporated by reference herein.

IV. Exemplary Surgical Procedure

Figure 19:
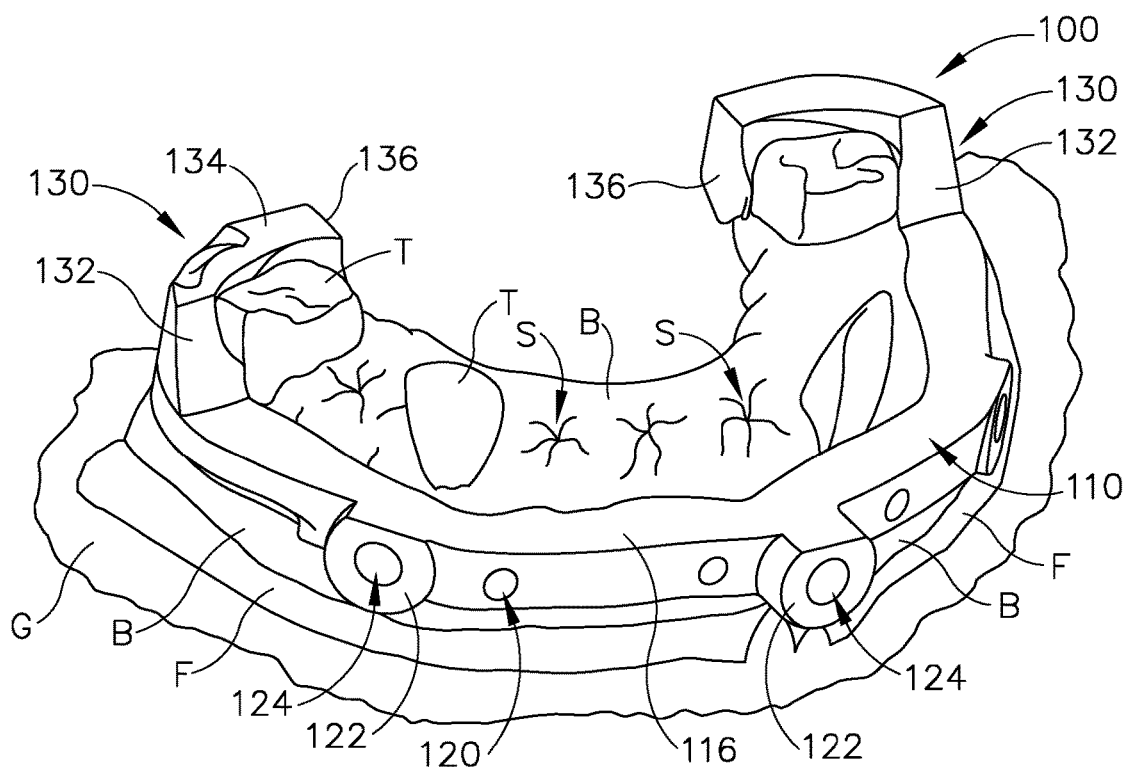
FIG. 19 depicts a perspective view of the bone foundation guide of FIG. 1 mounted to an alveolar ridge of a patient, before a bone reduction procedure.

FIGS. 19-23 show different stages of an exemplary surgical procedure in which bone foundation guide (100), strut assembly (200), and surgical guide (300) are used. As shown in FIG. 19, bone foundation guide (100) is positioned over an alveolar arch of a patient. In the present example, the alveolar arch is the mandibular alveolar arch, though the same procedure and similar equipment may be used on the maxillary alveolar arch. The only difference would be the bone foundation guide (100), strut assembly (200), and surgical guide (300) having customized configurations to fit on the maxillary alveolar arch.

As shown, before bone foundation guide (100) is installed, the clinician incises the gum (G) along the ridge of the alveolar arch and peels the gum (G) away, leaving flaps (F) to reveal bone (B). In the present example, bone foundation guide (100) rests entirely on bone (B), without being supported by any gum (G) tissue. As is also shown in FIG. 19, the patient in this case is missing several teeth, leaving behind sockets (S), with a few teeth (T) remaining. In order to fixedly secure bone foundation guide (100) to the bone (B), the clinician may drive pins, screws, or other fastener devices through passageways (124). Such fastener devices may be removable to facilitate removal of bone foundation guide (100) after the procedure is complete. With bone foundation guide (100) being installed on the bone (B), horizontal body portion (110) extends only along the buccal side of the alveolar arch. No horizontally extending portion of bone foundation guide (100) wraps along the lingual (or palatal) side of the alveolar arch. Lower surfaces (137) of upright body portions (130) rest on the upper ridge of the alveolar arch, thereby supplementing the structural support provided by the fastener devices that are disposed in passageways (124) and bone (B).

Figure 20:
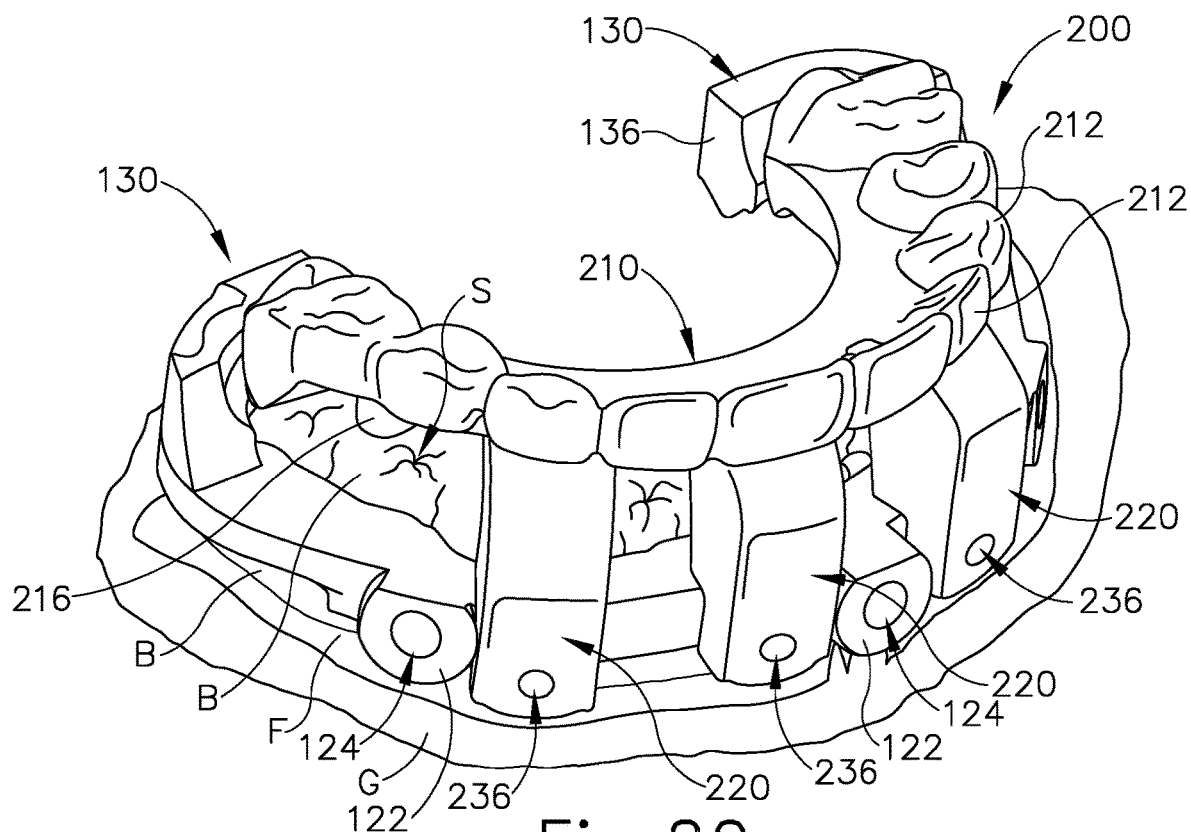
FIG. 20 depicts a perspective view of the assembled combination of the strut assembly of FIG. 4 and the bone foundation guide of FIG. 1 mounted to the alveolar ridge of FIG. 19, before the bone reduction procedure.
Figure 21:
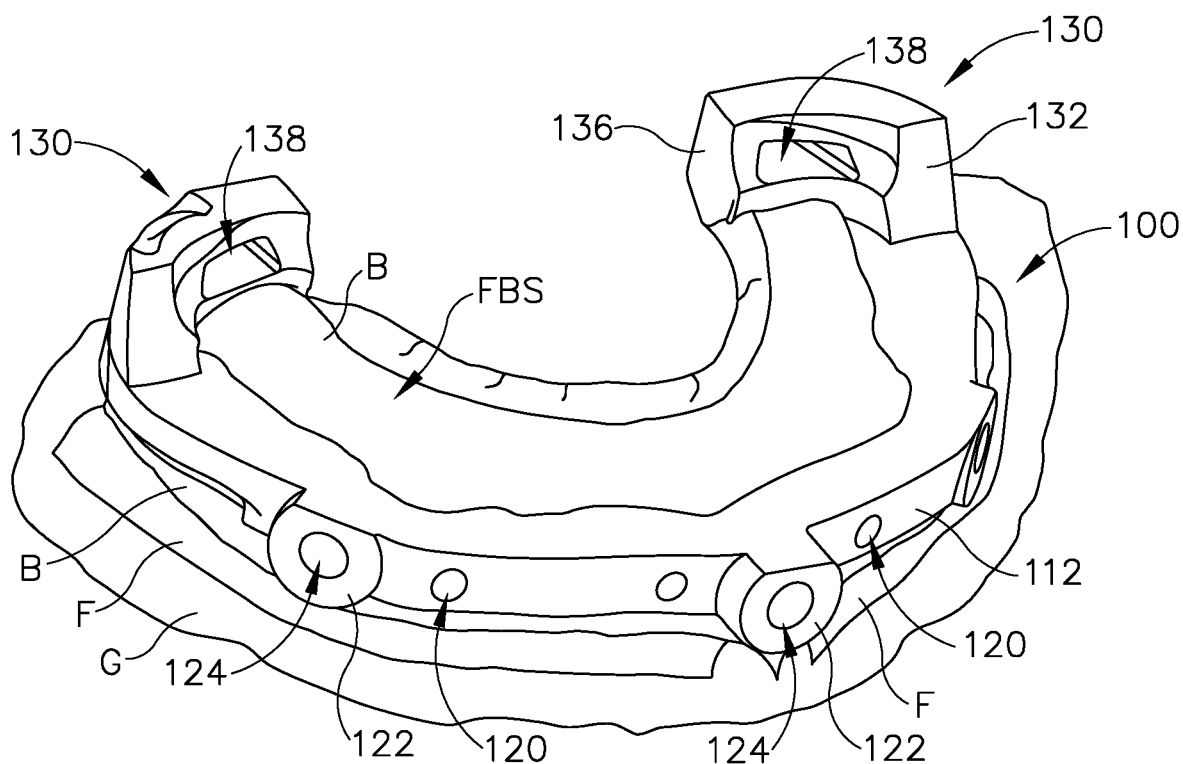
FIG. 21 depicts a perspective view of the bone foundation guide of FIG. 1 mounted to the alveolar ridge of FIG. 19, after the bone reduction procedure.

After securing bone foundation guide (100) to bone as shown in FIG. 19, the clinician may remove the remaining teeth (T) using any suitable techniques. The clinician may then secure strut assembly (200) to bone foundation guide (100) as shown in FIG. 20. As noted above, this may include inserting tabs (214) of strut assembly (200) into corresponding slots (138) of bone foundation guide (100). This also includes engaging horizontal body portion (110) with strut members (220), such that shelf portions (230) of strut members (220) receive horizontal body portion (110). At this stage, passageways (236) of strut members (220) are aligned with passageways (122) of horizontal body potion (110). The clinician may thus insert pins, screws, or other fastener devices through passageways (122, 236) to thereby secure strut assembly (200) to bone foundation guide (100). Also at this stage, studs (216) engage bone (B) at respective points along the alveolar ridge, thereby providing additional stability to strut assembly (200). Contact between studs (216) and bone (B) may further ensure the appropriate vertical and lateral positioning of strut assembly (200) relative to the alveolar ridge.

With strut assembly (200) coupled with bone foundation guide (100), the clinician may establish a state of occlusion between teeth (210) of strut assembly (200) and the teeth of the opposing alveolar ridge of the patient. This may be done as a preview to confirm that the teeth of the planned prosthetic will be an appropriate fit for the patient, since teeth (210) of strut assembly (200) match the placement and configuration of the teeth of the planned prosthetic. After confirming the appropriate fit, the clinician may remove strut assembly (200) from bone foundation guide (100).

After strut assembly (200) is removed from bone foundation guide (100), the physician may perform a bone reduction procedure on the alveolar ridge. This may include using a conventional bur or other cutting instrument to remove all portions of the bone (B) that protrudes above the upper surface (116) of bone foundation guide (100). In some instances, the physician may add material to bone (B). Such added material may be formed in part by bone material that has just been removed from the alveolar ridge. In either case, the end result of such procedures may look similar to the state shown in FIG. 21, in which a flush bone surface (FBS) is established. This flush bone surface (FBS) is substantially coplanar with the upper surface (116) of bone foundation guide (100), such that bone foundation guide (100) serves as a bone reduction guide. To achieve this flush bone surface (FBS), the clinician may use upper surface (116) to provide a visual cue, and in some cases structural support, for the instrumentation that is used to remove the bone (B) protruding above upper surface (116) and/or for the instrumentation that is used to add material to the bone (B) to achieve a flat, planar flush bone surface (FBS). Bone foundation guide (100) may thus provide structural and/or visual guidance for instrumentation during a bone reduction procedure.

Bone foundation guide (100) may also provide structural and/or visual guidance for a bone augmentation procedure. The degree of bone reduction and bone augmentation that is required may vary patient to patient, depending on the extent to which bone reduction and bone augmentation is required along the alveolar arch in order to achieve a flat, planar flush bone surface (FBS) that is flush with upper surface (116).

In some instances, a bur instrument guide is coupled with bone foundation guide (100), to assist in guiding a bur instrument relative to bone foundation guide (100) during a bone reduction procedure. Such a bur instrument guide may be constructed and operable in accordance with at least some of the teachings of U.S. Provisional Pat. App. No. 62/783, 286, entitled "Dental Bone Foundation Guide with Bur Instrument Guide Features," filed Dec. 21, 2018, the disclosure of which is incorporated by reference herein. Such scenarios may further include use of a modified version of bone foundation guide (100), where bone foundation guide (100) is modified to accommodate the bur instrument guide. Again, such modifications to bone foundation guide (100) may be provided in accordance with at least some of the teachings of U.S. Provisional Pat. App. No. 62/783,286.

Also in some instances, additional features may be coupled with bone foundation guide (100) to verify that planar flush bone surface (FBS) is in fact fully flush with upper surface (116). By way of example only, such additional features may be constructed and operable in accordance with at least some of the teachings of U.S. Provisional Pat. App. No. 62/793,926, entitled "Dental Bone Foundation Guide with Reduced Bone Level Verification," filed Jan. 18, 2019, the disclosure of which is incorporated by reference herein. Such scenarios may further include use of a modified version of bone foundation guide (100), where bone foundation guide (100) is modified to accommodate the additional features that are used to verify that planar flush bone surface (FBS) is in fact fully flush with upper surface (116). Again, such modifications to bone foundation guide (100) may be provided in accordance with at least some of the teachings of U.S. Provisional Pat. App. No. 62/793,926.

Figure 22:
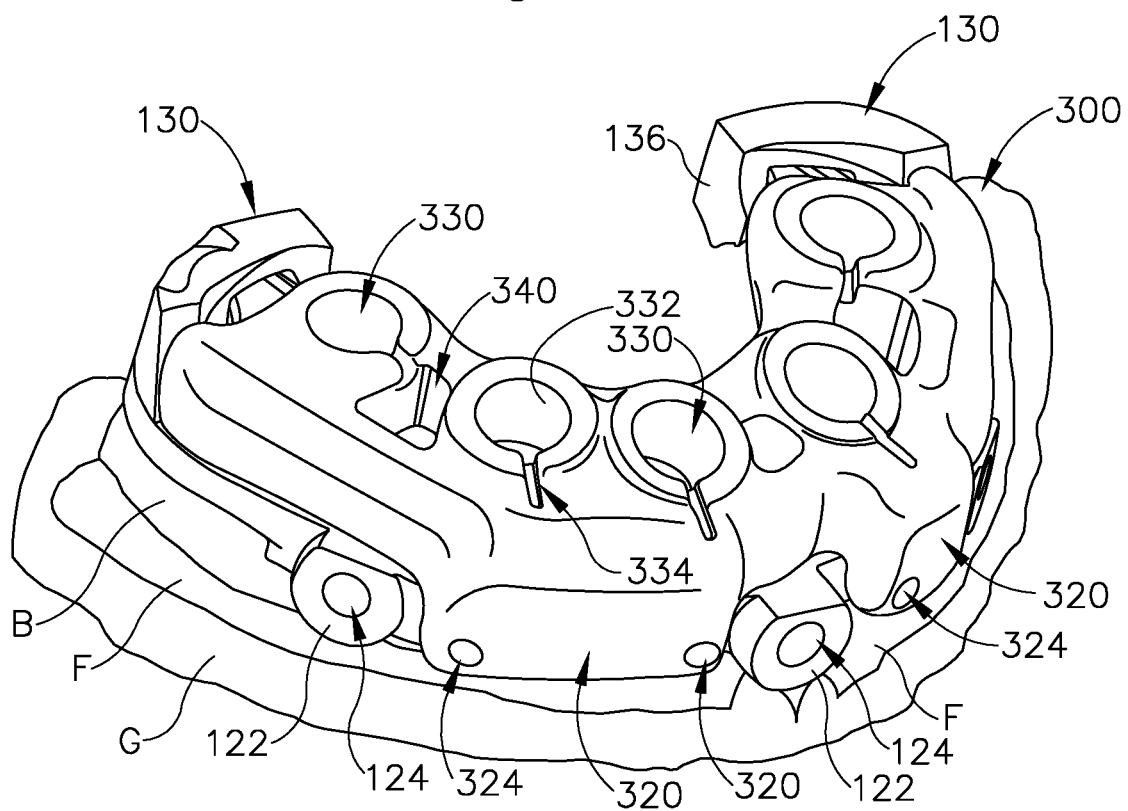
FIG. 22 depicts a perspective view of the assembled combination of the bone foundation guide of FIG. 1 and the surgical guide of FIG. 11 mounted to the alveolar ridge of FIG. 21.
Figure 23:
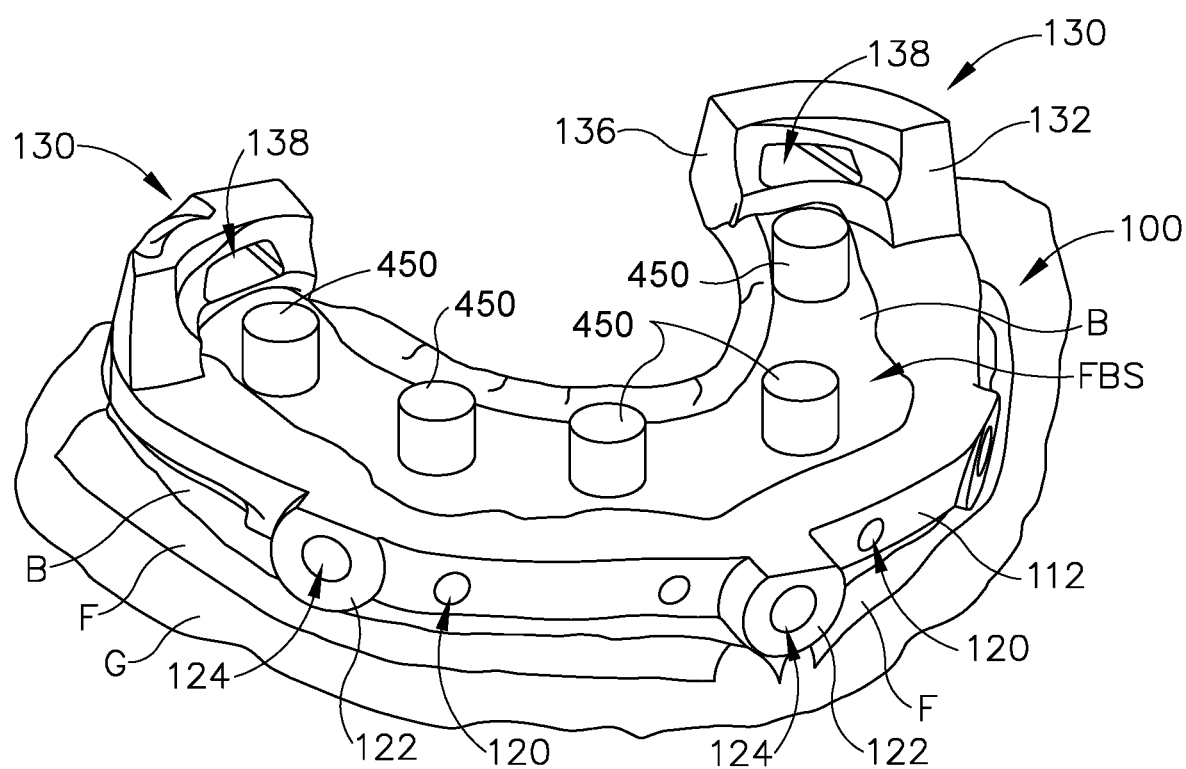
FIG. 23 depicts a perspective view of the alveolar ridge of FIG. 21 with a plurality of implant and abutment assemblies secured therein.

After completing the bone reduction (and perhaps bone augmentation) procedure, the clinician may couple surgical guide (300) with bone foundation guide (100), as shown in FIG. 22. As noted above, this may include inserting tabs (314) of surgical guide (300) into corresponding slots (138) of bone foundation guide (100). This also includes engaging upper surface (116) of horizontal body portion (110) with bottom surface (316) of horizontal body portion (310); and rear facing surfaces (322) of flange members (320) with front surface (112) of horizontal body portion (110). At this stage, passageways (324) of flange members (320) are aligned with passageways (122) of horizontal body potion (110). The clinician may thus insert pins, screws, or other fastener devices through passageways (122, 324) to thereby secure surgical guide (300) to bone foundation guide (100).

After surgical guide (300) and bone foundation guide (100) are coupled together, the clinician may insert a drill or other instrument successively in each passageway (330) to form openings in bone (B) to receive implants. The clinician may then insert the implants and associated installation instrumentation through passageways (330) to install the implants. After the implants are installed, the clinician may install abutments on the implants, again via passageways (330). After the abutments are installed, the clinician may remove surgical guide (300) and bone foundation guide (100) from the alveolar arch. The final result may appear similar to what is shown in FIG. 22. As shown in FIG. 22, surgical guide (300) has been removed from bone foundation guide (100), and implant and abutment assemblies (450) are left installed in the bone (B) of the alveolar ridge. While implant and abutment assemblies (450) are shown in schematic form in FIG. 22, various suitable forms that implant and abutment assemblies (450) may take will be apparent to those skilled in the art in view of the teachings herein.

In some versions of the procedure, before or after the implant and abutment assemblies (450) are installed, the clinician may also position a tissue-spacing gasket about the implant and abutment assemblies (450) and on the bone (B). The tissue-spacing gasket may have openings being formed through the tissue spacing gasket to accommodate the implant and abutment assemblies (450). The tissue-spacing gasket may be configured to mimic the thickness of the gum (G) tissue forming flaps (F). A dental prosthetic may then be positioned over the tissue spacing gasket and the installed implant and abutment assemblies (450) to confirm that the dental prosthetic will properly receive the implant and abutment assemblies (450); and to confirm that the dental prosthetic is otherwise properly configured for the patient. If the configuration is confirmed as appropriate, the dental prosthetic and tissue spacing gasket are removed. Then bone foundation guide (100) is removed. After bone foundation guide (100) is removed, the flaps (F) of gum (G) are positioned back over the bone (B) and around the installed implant and abutment assemblies (450) and are then sutured in place. After the gum (G) sufficiently heals (or immediately after the flaps (F) are repositioned over the bone (B) and sutured in place), the dental prosthetic is secured to implant and abutment assemblies (450), on top of the gum (G) tissue.

V. Exemplary Dental Prosthetic

In some conventional procedures, a clinician may need to first install a temporary or provisional dental prosthetic after completing the steps described above with reference to FIGS. 19-23. The clinician may then wait for some substantial period of time (e.g., 4-6 months), then remove the provisional prosthetic and install a final dental prosthetic. This process may further be complicated by the need for performing additional adjustments before completing the installation of the final prosthetic. This process of using a provisional dental prosthetic and then a final dental prosthetic may result in a substantial amount of time a patient needs to spend in such procedures, a substantial expenditure on materials, and a substantial expenditure of labor costs. It may therefore be desirable to provide a procedure where the bone reduction procedure is performed with enough precision to minimize or eliminate the need for fine tuning; and where the final dental prosthetic may be installed immediately without needing to first use a provisional dental prosthetic.

Figure 24:
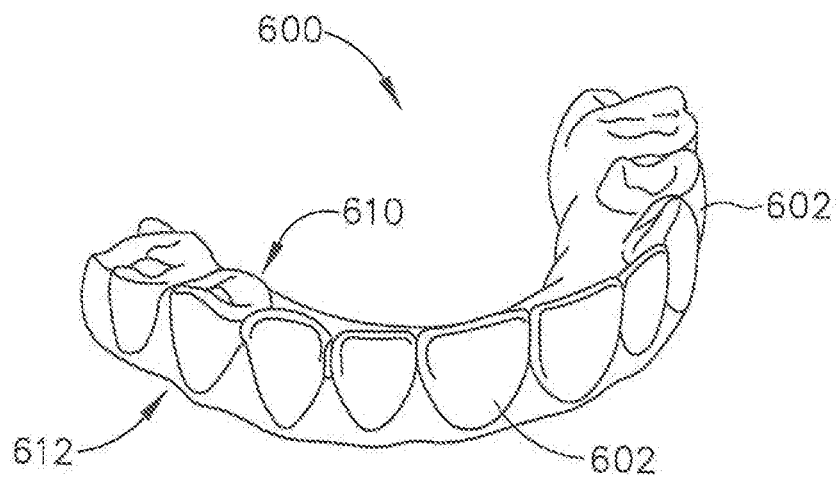
FIG. 24 depicts a perspective view of an exemplary dental prosthetic.
Figure 25:
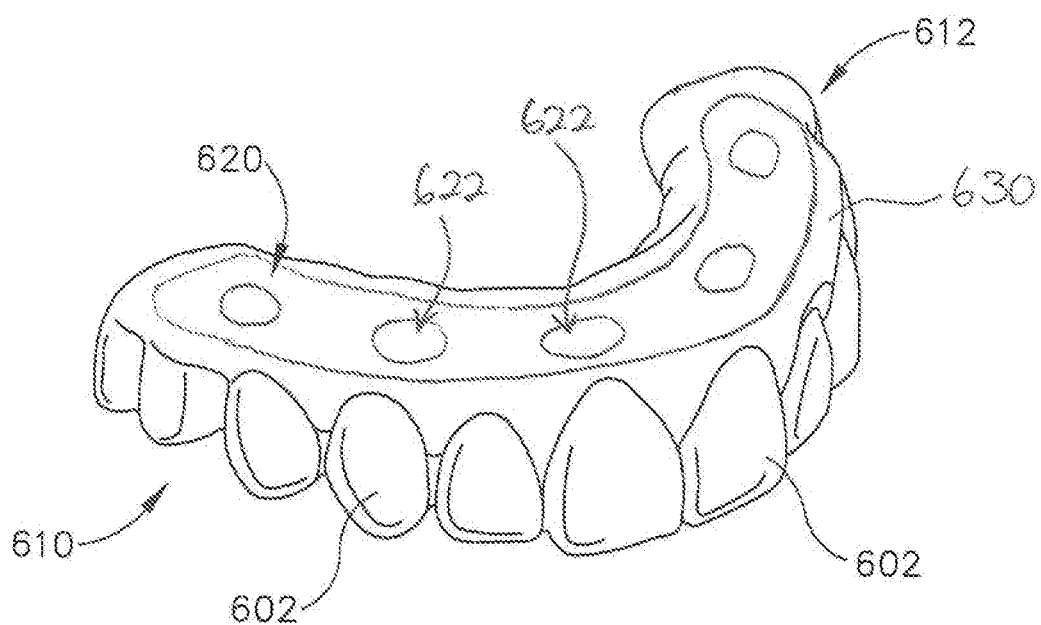
FIG. 25 depicts another perspective view of the dental prosthetic of FIG. 24.
Figure 26:
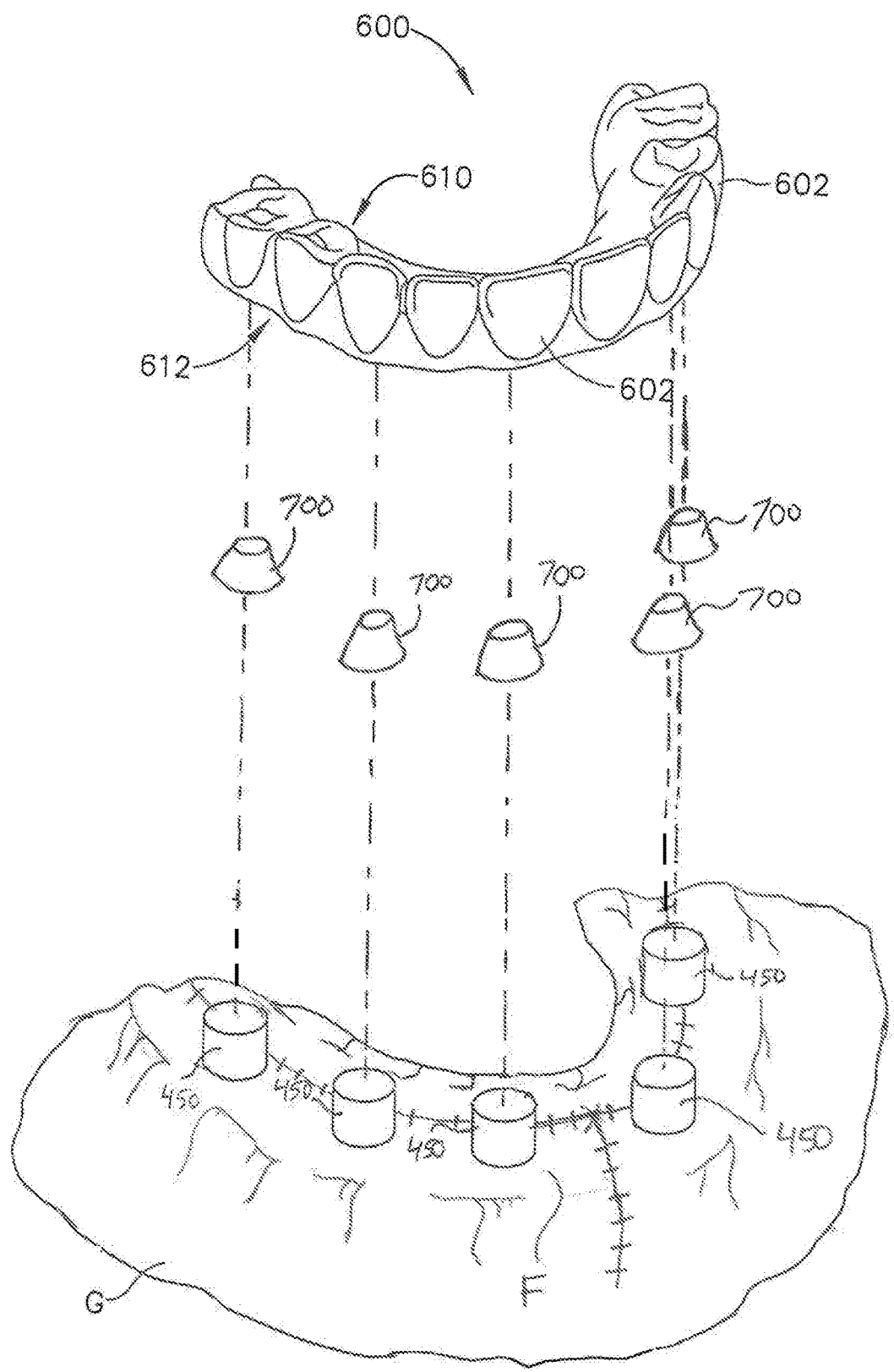
FIG. 26 depicts an exploded perspective view of the dental prosthetic of FIG. 24 positioned over the alveolar ridge of FIG. 23, with inserts positioned between the dental prosthetic and the alveolar ridge.

The following describes an example of a dental prosthetic and associated process where a final dental prosthetic may be installed immediately after completing the steps described above with reference to FIGS. 19-23, without the need for using a temporary or provisional dental prosthetic. In particular, FIGS. 24-26 show a dental prosthetic (600) that includes a horizontally extending body (610) that forms an arch that is configured to match the alveolar arch of the patient in which dental prosthetic (600) is to be installed. Dental prosthetic (600) further includes a full set of representations (602) of teeth. The underside (612) of body (610) includes a base (620) with a plurality of recesses (622) formed therein. Recesses (622) are configured to receive inserts (700) as described in greater detail below. Each recess (622) includes a concave countersink leading to a passageway that passes through dental prosthetic (600). For instance, each passageway may further pass through corresponding occlusal surfaces or other portions of representations (602) of teeth, thereby providing a screw access hole as will be described in greater detail below.

In the present example, dental prosthetic (600) is formed of nanoceramic material. Nanoceramic material may provide a combination of benefits making it preferable over other materials that are conventionally used to form dental prosthetics. For instance, nanoceramic may provide enough durability to allow dental prosthetic (600) to be used as a final prosthetic, such that a patient with a nanoceramic version of dental prosthetic (600) may use dental prosthetic (600) on a daily basis, just like they would use a normal healthy set of teeth, for the rest of their lives. Moreover, nanoceramic may enable crafting of dental prosthetic (600) with sufficient aesthetics such that dental prosthetic (600) may provide the appearance of natural teeth and gums, resulting in long term patient satisfaction. Nanoceramic may also provide dental prosthetic (600) with enough structural flexibility such that dental prosthetic may be adjusted during the installation procedure to properly fit the bite of the patient, without needing to send dental prosthetic (600) back to a dental laboratory in order to have such adjustments made.

In some versions, base (620) includes a polymer over the nanoceramic material, to provide a softened fit with the tissue against which base (620) is seated. By way of example only, base (620) may include TriLor® high performance polymer material by Preat Corporation of Grover Beach, Calif. Alternatively, any other suitable material(s) may be used to form base (620). Also in some versions, the gum portion (630) of dental prosthetic (600) may include a pink gingiva resin layer over the nanoceramic material, to provide an appearance of natural gum tissue. In addition, all or part of dental prosthetic (600) may be coated with an acrylic material to provide an aesthetic glossy surface that further protects dental prosthetic (600). By way of example only, the acrylic material may include Optiglaze™ coating by GC America Inc. of Alsip, Ill. Other suitable materials that may be incorporated into dental prosthetic (600) will be apparent to those skilled in the art in view of the teachings herein.

By way of further example only, dental prosthetic (600) may be formed using rapid prototyping equipment (e.g., 3D printing or other additive manufacturing, etc.), based on a three-dimensional digital model as noted above. Various suitable ways in which dental prosthetic (600) may be formed will be apparent to those skilled in the art in view of the teachings herein.

As shown in FIG. 26 dental prosthetic (600) may be secured to implant and abutment assemblies (450) via a set of copings or inserts (700). As noted above, each insert (700) is configured to fit in a corresponding recess (622) on base (620). Inserts (700) of the present example are formed of titanium and are frusto-conical in shape. By way of example only, inserts (700) may comprise DESS Ti Bases by DESS-USA of Granite Bay, Calif. Alternatively, inserts (700) may have any other suitable configuration.

Before inserts (700) are used to secure dental prosthetic (600) to implant and abutment assemblies (450), inserts (700) are first secured to dental prosthetic (600) using a "pickup" process. This process begins after the flaps (F) of gum (G) are positioned back over the bone (B) and around the installed implant and abutment assemblies (450); and the flaps (F) are sutured in place as shown in FIG. 26. To begin the "pickup" process, the clinician first secures inserts (700) to implant and abutment assemblies (450) using conventional screws. The clinician then applies a cement to each recess (622). By way of example only, the cement may comprise Rely-X™ Unicem 2 Self-Adhesive Resin Cement by 3M Company of St. Paul, Minn. This particular cement may be compatible with both the nanoceramic material of dental prosthetic (600) and implant and abutment assemblies (450), providing enough durability to enable dental prosthetic (600) to remain installed and used like natural teeth for the rest of the patient's life.

After the cement has been applied to each recess (622), dental prosthetic (600) may be pressed onto the combination of inserts (700) and implant and abutment assemblies (450), thereby seating inserts (700) in recesses (622). The clinician may then wait a predetermined period of time to allow the cement to cure, thereby adhering inserts (700) to dental prosthetic (600). Once inserts (700) are adhered to dental prosthetic (600) by the cement, the clinician may access the screws via screw access holes (not shown) in dental prosthetic (600). As noted above, such screw access holes may be formed through occlusal surfaces or other portions of representations (602) of teeth. The clinician may then remove the screws. With the screws removed, the clinician may then pull dental prosthetic (600) away from implant and abutment assemblies (450). Due to the cured cement, inserts (700) will remain firmly secured in corresponding recesses (622), leaving behind implant and abutment assemblies (450). This "pickup" process may ensure that inserts (700) are properly positioned and aligned in dental prosthetic (600), such that dental prosthetic (600) will subsequently appropriately couple with implant and abutment assemblies (450) as described in greater detail below. After completing the "pickup" process, the clinician may remove any excess cement and/or perform any other necessary cleanup procedures on dental prosthetic (600).

In some instances, it may be desirable to have a backup dental prosthetic. Such a backup dental prosthetic may be configured just like dental prosthetic (600); but may be formed of a different material. By way of example only, a backup dental prosthetic may be formed of poly(methyl methacrylate) (PMMA). In versions where a backup dental prosthetic us provided, the clinician may perform the same kind of "pickup" process as described above in order to secure inserts (700) to the backup dental prosthetic.

After completing the "pickup" process for dental prosthetic (600) and performing any necessary cleanup on dental prosthetic (600), and after optionally performing the same processes on a backup dental prosthetic, the clinician may then secure dental prosthetic (600) to implant and abutment assemblies (450) using screws inserted through the screw access openings of dental prosthetic. Such screws may firmly secure inserts (700) directly to implant and abutment assemblies (450). The clinician may then fill the screw access openings with any suitable material using known techniques. At this point, the process may be complete, and the patient may use dental prosthetic (600) like they would use natural teeth; and it may not be necessary to ever need to replace dental prosthetic (600).

In some instances, a patient may experience tissue or bone loss after dental prosthetic (600) is installed using the process described above. In the event that this occurs, the clinician may rough up the tissue contact surface adjacent to underside (612), then inject a material to fill in any gaps between the tissue and the underside of dental prosthetic (600). By way of example only, such material may include a dental reline material or a dental impression material. The clinician may then remove dental prosthetic (600) with the injected material adhered to dental prosthetic (600). Dental prosthetic (600) may then be sent to a dental laboratory, which can then reprocess the material into dental prosthetic (600). After the dental laboratory has reconfigured dental prosthetic (600) in this manner, the reconfigured dental prosthetic (600) may be re-installed in the patient's mouth using the technique described above. While dental prosthetic (600) is being reconfigured at the dental laboratory, the patient may be fitted with the backup dental prosthetic as described above, such that the backup dental prosthetic may remain secured to implant and abutment assemblies (450) in the absence of dental prosthetic (600).

While dental prosthetic (600) of the present example is in the form of a full arch restoration (i.e., full bridge), the teachings herein may be readily applied to scenarios where dental prosthetic (600) is just a partial restoration/bridge.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of installing a dental prosthetic device, the method comprising: (a) securing a first guide member to an alveolar arch in a mouth of a patient; (b) utilizing the first guide member to achieve a substantially planar bone surface along the alveolar arch; (c) coupling a second guide member with the first guide member; (d) utilizing the second guide member to install one or more implants in the alveolar arch through substantially planar bone surface; and (e) securing a dental prosthetic to the one or more implants, wherein the dental prosthetic comprises a nanoceramic material.

Example 2

The method of Example 1, wherein the first guide member comprises: (i) a horizontal body portion, wherein the horizontal body portion has an arcuate configuration, wherein the horizontal body portion includes: (A) a first horizontal surface, wherein the first horizontal surface is flat, (B) a front surface, (C) a rear surface, wherein the rear surface is configured to closely mate with a front-facing bone structure of the alveolar arch of a patient, and (D) a second horizontal surface, wherein the front and rear surfaces extend between the first and second horizontal surfaces, (ii) a first upright body portion positioned at one end of the horizontal body portion, wherein the first upright body portion includes a first inwardly extending portion, wherein a first engagement surface of the first inwardly extending portion is configured to rest on a ridge of the alveolar arch of the patient, and (iii) a second upright body portion positioned at another end of the horizontal body portion, wherein the second upright body portion includes a second inwardly extending portion, wherein a second engagement surface of the second inwardly extending portion is configured to rest on a ridge of the alveolar arch of the patient, wherein the first guide member lacks a component configured to extend along a lingual or palatal side of the alveolar arch of the patient.

Example 3

The method of Example 2, wherein the first upright body portion defines a first slot, wherein the second upright body portion defines a second slot.

Example 4

The method of any one or more of Examples 2 through 3, wherein the horizontal body portion defines a plurality of openings extending from the front surface to the rear surface.

Example 5

The method of any one or more of Examples 2 through 4, wherein the first engagement surface is configured to closely mate with a first bone structure of the alveolar ridge of the patient, wherein the second engagement surface is configured to closely mate with a second bone structure of the alveolar ridge of the patient.

Example 6

The method of any one or more of Examples 1 through 5, further comprising: (a) mounting a strut assembly to the first guide member to confirm proper placement of the first guide member; and (b) removing the strut assembly from the first guide member before coupling the second guide member to the first guide member.

Example 7

The method of Example 6, wherein the strut assembly comprises: (i) a horizontal body portion, wherein the horizontal body portion of the strut assembly has an arcuate configuration generally corresponding to the arcuate configuration of the first guide member, (ii) a set of strut members configured to engage a horizontal body portion of the first guide member, and (iii) a set of three-dimensional representations of teeth, wherein the strut members are configured to position the teeth at a predetermined distance from a first horizontal surface of the first guide member.

Example 8

The method of Example 7, wherein the strut members include shelf portions, wherein the shelf portions are configured to engage the first horizontal surface and a front surface of the first guide member.

Example 9

The method of any one or more of Examples 7 through 8, wherein the first guide member includes a first set of openings, wherein the strut members include a second set of openings, wherein the second set of openings is configured to align with the first set of openings, wherein the first and second sets of openings are configured to receive fasteners when the second set of openings is aligned with the first set of openings.

Example 10

The method of any one or more of Examples 7 through 9, wherein the horizontal body portion of the strut assembly defines a pair of tabs at each end of the arcuate configuration, wherein the first guide member defines a pair of slots, wherein the slots are configured to receive the tabs.

Example 11

The method of Example 10, wherein the slots are defined by first and second upright body portions of the first guide member.

Example 12

The method of any one or more of Examples 6 through 11, wherein the strut assembly further includes one or more studs projecting from the horizontal body portion of the strut assembly opposite to the teeth, wherein the studs are configured to engage corresponding regions of the alveolar ridge of the patient.

Example 13

The method of any one or more of Examples 1 through 12, wherein the second guide member comprises: (i) a horizontal body portion, wherein the horizontal body portion of the second guide member has an arcuate configuration generally corresponding to an arcuate configuration of the first guide member, (ii) a set of flange members configured to engage a horizontal body portion of the first guide member, and (iii) a set of guide passageways.

Example 14

The method of Example 13, wherein the horizontal body portion of the second guide member has a horizontal surface configured to engage a first horizontal surface of the horizontal body portion of the first guide member.

Example 15

The method of any one or more of Examples 13 through 14, wherein each flange member has a rear surface configured to engage a front surface of the horizontal body portion of the first guide member.

Example 16

The method of any one or more of Examples 13 through 15, wherein the horizontal body portion of the first guide member includes a first set of openings, wherein the flange members include a second set of openings, wherein the second set of openings is configured to align with the first set of openings, wherein the first and second sets of openings are configured to receive fasteners when the second set of openings is aligned with the first set of openings.

Example 17

The method of any one or more of Examples 13 through 16, wherein the horizontal body portion of the second guide member defines a pair of tabs at each end of the arcuate configuration, wherein the first guide member defines a pair of slots, wherein the slots are configured to receive the tabs.

Example 18

The method of Example 17, wherein the slots are defined by first and second upright body portions of the first guide member.

Example 19

The method of any one or more of Examples 1 through 18, wherein the dental prosthetic comprises a bridge.

Example 20

The method of Example 19, wherein the bridge comprises a full arch bridge spanning the full alveolar arch.

Example 21

The method of any one or more of Examples 1 through 20, wherein the dental prosthetic includes a base having a polymer material.

Example 22

The method of any one or more of Examples 1 through 21, wherein the dental prosthetic includes a pink gingiva resin layer over the nanoceramic material.

Example 23

The method of any one or more of Examples 1 through 22, wherein the dental prosthetic comprises an acrylic material layer over the nanoceramic material.

Example 24

The method of any one or more of Examples 1 through 23, wherein the dental prosthetic includes one or more metallic inserts in the nanoceramic material, wherein the dental prosthetic is secured to the one or more implants via the one or more metallic inserts.

Example 25

The method of Example 24, further comprising securing one or more abutments to the one or more implants, wherein securing the dental prosthetic to the one or more implants comprises securing the one or more metallic inserts to the one or more abutments.

Example 26

The method of Example 25, wherein securing the one or more metallic inserts to the one or more abutments comprises: (i) inserting one or more screws through the dental prosthetic, and (ii) securing the one or more metallic inserts to the one or more abutments via the one or more inserted screws.

Example 27

The method of any one or more of Examples 24 through 26, further comprising: (i) securing the one or metallic inserts to the one or more abutments, before the one or more metallic inserts are secured to the dental prosthetic, (ii) applying cement in one or more recesses formed in the dental prosthetic, (iii) positioning the dental prosthetic on the one or more metallic inserts such that the one or more metallic inserts are received in the one or more recesses formed in the dental prosthetic, and (iv) waiting for the cement to cure such that the one or more metallic inserts are secured to the dental prosthetic via the cement.

Example 28

The method of Example 27, further comprising removing the one or more metallic inserts and the dental prosthetic from the one or more abutments, wherein the one or more metallic inserts remain secured to the dental prosthetic via the cement after removing the one or more metallic inserts and the dental prosthetic from the one or more abutments.

Example 29

The method of Example 28, further comprising removing excess cement material from the dental prosthetic after removing the one or more metallic inserts and the dental prosthetic from the one or more abutments.

Example 30

The method of Example 29, further comprising securing the dental prosthetic and the one or more metallic inserts to the abutments after removing the excess cement material.

Example 31

The method of any one or more of Examples 28 through 30, further comprising: (i) securing another one or metallic inserts to the one or more abutments after removing the one or more metallic inserts and the dental prosthetic from the one or more abutments, (ii) applying cement in one or more recesses formed in a second dental prosthetic, (iii) positioning the second dental prosthetic on the another one or more metallic inserts such that the another one or more metallic inserts are received in the one or more recesses formed in the second dental prosthetic, and (iv) waiting for the cement to cure such that the another one or more metallic inserts are secured to the second dental prosthetic via the cement.

Example 32

The method of Example 31, further comprising removing the another one or more metallic inserts and the second dental prosthetic from the one or more abutments, wherein the another one or more metallic inserts remain secured to the second dental prosthetic via the cement after removing the another one or more metallic inserts and the second dental prosthetic from the one or more abutments.

Example 33

The method of Example 32, further comprising securing the dental prosthetic and the one or more metallic inserts to the abutments after removing the another one or more metallic inserts and the second dental prosthetic from the one or more abutments.

Example 34

The method of any one or more of Examples 31 through 33, wherein the second dental prosthetic comprises poly (methyl methacrylate).

Example 35

The method of any one or more of Examples 1 through 34, further comprising injecting a dental reline material in one or more gaps defined between gum tissue of the alveolar arch and a corresponding surface of the dental prosthetic.

Example 36

The method of Example 35, further comprising modifying a configuration of the dental prosthetic based on the injected dental reline material.

Example 37

The method of any one or more of Examples 1 through 36, further comprising injecting a dental impression material in one or more gaps defined between gum tissue of the alveolar arch and a corresponding surface of the dental prosthetic.

Example 38

The method of Example 37, further comprising modifying a configuration of the dental prosthetic based on the injected dental impression material.

Example 39

The method of any one or more of Examples 1 through 38, wherein utilizing the first guide member to achieve a substantially planar bone surface along the alveolar arch comprises removing bone protruding past a plane defined by a horizontal surface of the first guide member.

Example 40

The method of any one or more of Examples 1 through 39, wherein utilizing the first guide member to achieve a substantially planar bone surface along the alveolar arch comprises adding bone augmentation material bone recessed below a plane defined by a horizontal surface of the first guide member.

Example 41

An apparatus, comprising: (a) a first guide member, the first guide member being configured to be secured to an alveolar arch in a mouth of a patient; (b) a second guide member, the second guide member being configured to couple with the first guide member while the first guide member is secured to the alveolar arch, the second guide member being configured to guide installation of one or more implants in the alveolar arch; and (c) a dental prosthetic, the dental prosthetic being configured to be secured to the alveolar arch by at least one or more implants installed in the alveolar arch, the dental prosthetic comprising nano-ceramic material.

Example 42

The apparatus of Example 41, wherein the first guide member comprises: (i) a horizontal body portion, wherein the horizontal body portion has an arcuate configuration, wherein the horizontal body portion includes: (A) a first horizontal surface, wherein the first horizontal surface is flat, (B) a front surface, (C) a rear surface, wherein the rear surface is configured to closely mate with a front-facing bone structure of the alveolar arch, and (D) a second horizontal surface, wherein the front and rear surfaces extend between the first and second horizontal surfaces, (ii) a first upright body portion positioned at one end of the horizontal body portion, wherein the first upright body portion includes a first inwardly extending portion, wherein a first engagement surface of the first inwardly extending portion is configured to rest on a ridge of the alveolar arch, and (iii) a second upright body portion positioned at another end of the horizontal body portion, wherein the second upright body portion includes a second inwardly extending portion, wherein a second engagement surface of the second inwardly extending portion is configured to rest on a ridge of the alveolar arch, wherein the first guide member lacks a component configured to extend along a lingual or palatal side of the alveolar arch.

Example 43

The apparatus of Example 42, wherein the first upright body portion defines a first slot, wherein the second upright body portion defines a second slot.

Example 44

The apparatus of Examples 42 through 43, wherein the horizontal body portion defines a plurality of openings extending from the front surface to the rear surface.

Example 45

The apparatus of any one or more of Examples 42 through 44, wherein the first engagement surface is configured to closely mate with a first bone structure of the alveolar ridge, wherein the second engagement surface is configured to closely mate with a second bone structure of the alveolar ridge.

Example 46

The apparatus of any one or more of Examples 41 through 45, further comprising a strut assembly, the strut assembly being configured to couple with the first guide member to confirm proper placement of the first guide member.

Example 47

The apparatus of Example 46, wherein the strut assembly comprises: (i) a horizontal body portion, wherein the horizontal body portion of the strut assembly has an arcuate configuration generally corresponding to the arcuate configuration of the first guide member, (ii) a set of strut members configured to engage a horizontal body portion of the first guide member, and (iii) a set of three-dimensional representations of teeth, wherein the strut members are configured to position the teeth at a predetermined distance from a first horizontal surface of the first guide member.

Example 48

The apparatus of Example 47, wherein the strut members include shelf portions, wherein the shelf portions are configured to engage the first horizontal surface and a front surface of the first guide member.

Example 49

The apparatus of any one or more of Examples 47 through 48, wherein the first guide member includes a first set of openings, wherein the strut members include a second set of openings, wherein the second set of openings is configured to align with the first set of openings, wherein the first and second sets of openings are configured to receive fasteners when the second set of openings is aligned with the first set of openings.

Example 50

The apparatus of any one or more of Examples 47 through 49, wherein the horizontal body portion of the strut assembly defines a pair of tabs at each end of the arcuate configuration, wherein the first guide member defines a pair of slots, wherein the slots are configured to receive the tabs.

Example 51

The apparatus of Example 50, wherein the slots are defined by first and second upright body portions of the first guide member.

Example 52

The apparatus of any one or more of Examples 46 through 51, wherein the strut assembly further includes one or more studs projecting from the horizontal body portion of the strut assembly opposite to the teeth, wherein the studs are configured to engage corresponding regions of the alveolar ridge of the patient.

Example 53

The apparatus of any one or more of Examples 41 through 52, wherein the second guide member comprises: (i) a horizontal body portion, wherein the horizontal body portion of the second guide member has an arcuate configuration generally corresponding to an arcuate configuration of the first guide member, (ii) a set of flange members configured to engage a horizontal body portion of the first guide member, and (iii) a set of guide passageways.

Example 54

The apparatus of Example 53, wherein the horizontal body portion of the second guide member has a horizontal surface configured to engage a first horizontal surface of the horizontal body portion of the first guide member.

Example 55

The apparatus of any one or more of Examples 53 through 54, wherein each flange member has a rear surface configured to engage a front surface of the horizontal body portion of the first guide member.

Example 56

The apparatus of any one or more of Examples 53 through 55, wherein the horizontal body portion of the first guide member includes a first set of openings, wherein the flange members include a second set of openings, wherein the second set of openings is configured to align with the first set of openings, wherein the first and second sets of openings are configured to receive fasteners when the second set of openings is aligned with the first set of openings.

Example 57

The apparatus of any one or more of Examples 53 through 56, wherein the horizontal body portion of the second guide member defines a pair of tabs at each end of the arcuate configuration, wherein the first guide member defines a pair of slots, wherein the slots are configured to receive the tabs.

Example 58

The apparatus of Example 57, wherein the slots are defined by first and second upright body portions of the first guide member.

Example 59

The apparatus of any one or more of Examples 41 through 58, wherein the dental prosthetic comprises a bridge.

Example 60

The apparatus of Example 59, wherein the bridge comprises a full arch bridge spanning the full alveolar arch.

Example 61

The apparatus of any one or more of Examples 41 through 60, wherein the dental prosthetic includes a base having a polymer material.

Example 62

The apparatus of any one or more of Examples 41 through 61, wherein the dental prosthetic includes a pink gingiva resin layer over the nanoceramic material.

Example 63

The apparatus of any one or more of Examples 41 through 62, wherein the dental prosthetic comprises an acrylic material layer over the nanoceramic material.

Example 64

The apparatus of any one or more of Examples 41 through 63, further comprising one or more metallic inserts, wherein the dental prosthetic is configured to be secured to the one or more implants via the one or more metallic inserts.

Example 65

The apparatus of Example 64, further comprising one or more abutments, wherein the one or more abutments are configured to be secured to the one or more implants, wherein the one or more metallic inserts are configured to be secured to the one or more abutments, wherein the dental prosthetic is configured to be secured to the one or more implants via the one or more metallic inserts and the one or more abutments.

Example 66

The apparatus of any one or more of Examples 41 through 65, further comprising a second dental prosthetic, the second dental prosthetic being configured to be secured to the alveolar arch by at least one or more implants installed in the alveolar arch, the second dental prosthetic comprising poly (methyl methacrylate).

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of installing a dental prosthetic device, the method comprising:
   (a) securing a first guide member to an alveolar arch in a mouth of a patient;
   (b) utilizing the first guide member to achieve a substantially planar bone surface along the alveolar arch;
   (c) mounting a strut assembly to the first guide member to confirm proper placement of the first guide member, wherein the strut assembly comprises:
      (i) a horizontal body portion, wherein the horizontal body portion of the strut assembly has an arcuate configuration generally corresponding to an arcuate configuration of the first guide member,
      (ii) a set of strut members configured to engage a horizontal body portion of the first guide member, and
      (iii) a set of three-dimensional representations of teeth, wherein the strut members are configured to position the teeth at a predetermined distance from a first horizontal surface of the first guide member;
   (d) removing the strut assembly from the first guide member;
   (e) coupling a second guide member with the first guide member after removing the strut assembly from the first guide member;
   (f) utilizing the second guide member to install one or more implants in the alveolar arch through substantially planar bone surface; and
   (g) securing a dental prosthetic to the one or more implants, wherein the dental prosthetic comprises a nanoceramic material.

2. The method of claim 1, wherein the first guide member comprises:
   (i) a horizontal body portion, wherein the horizontal body portion has an arcuate configuration, wherein the horizontal body portion includes:
      (A) a first horizontal surface, wherein the first horizontal surface is flat,
      (B) a front surface,
      (C) a rear surface, wherein the rear surface is configured to closely mate with a front-facing bone structure of the alveolar arch of a patient, and
      (D) a second horizontal surface,
      wherein the front and rear surfaces extend between the first and second horizontal surfaces,
   (ii) a first upright body portion positioned at one end of the horizontal body portion, wherein the first upright body portion includes a first inwardly extending portion, wherein a first engagement surface of the first inwardly extending portion is configured to rest on a ridge of the alveolar arch of the patient, and
   (iii) a second upright body portion positioned at another end of the horizontal body portion, wherein the second upright body portion includes a second inwardly extending portion, wherein a second engagement surface of the second inwardly extending portion is configured to rest on a ridge of the alveolar arch of the patient,
   wherein the first guide member lacks a component configured to extend along a lingual or palatal side of the alveolar arch of the patient.

3. The method of claim 1, wherein the second guide member comprises:
   (i) a horizontal body portion, wherein the horizontal body portion of the second guide member has an arcuate configuration generally corresponding to an arcuate configuration of the first guide member,
   (ii) a set of flange members configured to engage a horizontal body portion of the first guide member, and
   (iii) a set of guide passageways.

4. The method of claim 3, wherein the horizontal body portion of the second guide member defines a pair of tabs at each end of the arcuate configuration, wherein the first guide member defines a pair of slots, wherein the slots are configured to receive the tabs.

5. The method of claim 4, wherein the slots are defined by first and second upright body portions of the first guide member.

6. The method of claim 1, wherein the dental prosthetic comprises a full arch bridge spanning the full alveolar arch.

7. The method of claim 1, wherein the dental prosthetic includes one or more metallic inserts in the nanoceramic material, wherein the dental prosthetic is secured to the one or more implants via the one or more metallic inserts, the method further comprising securing one or more abutments to the one or more implants, wherein securing the dental prosthetic to the one or more implants comprises securing the one or more metallic inserts to the one or more abutments, wherein securing the one or more metallic inserts to the one or more abutments comprises:
   (i) inserting one or more screws through the dental prosthetic, and
   (ii) securing the one or more metallic inserts to the one or more abutments via the one or more inserted screws.

8. The method of claim 7, further comprising:
   (i) securing the one or more metallic inserts to the one or more abutments, before the one or more metallic inserts are secured to the dental prosthetic, (ii) applying cement in one or more recesses formed in the dental prosthetic,
(iii) positioning the dental prosthetic on the one or more metallic inserts such that the one or more metallic inserts are received in the one or more recesses formed in the dental prosthetic,
(iv) waiting for the cement to cure such that the one or more metallic inserts are secured to the dental prosthetic via the cement,
(v) removing the one or more metallic inserts and the dental prosthetic from the one or more abutments, wherein the one or more metallic inserts remain secured to the dental prosthetic via the cement after removing the one or more metallic inserts and the dental prosthetic from the one or more abutments, and
(vi) securing the dental prosthetic and the one or more metallic inserts to the one or more abutments.

9. The method of claim 8, further comprising:
(i) securing another one or metallic inserts to the one or more abutments after removing the one or more metallic inserts and the dental prosthetic from the one or more abutments,
(ii) applying cement in one or more recesses formed in a second dental prosthetic,
(iii) positioning the second dental prosthetic on the another one or more metallic inserts such that the another one or more metallic inserts are received in the one or more recesses formed in the second dental prosthetic,
(iv) waiting for the cement to cure such that the another one or more metallic inserts are secured to the second dental prosthetic via the cement; and
(v) removing the another one or more metallic inserts and the second dental prosthetic from the one or more abutments, wherein the another one or more metallic inserts remain secured to the second dental prosthetic via the cement after removing the another one or more metallic inserts and the second dental prosthetic from the one or more abutments,
wherein the second dental prosthetic comprises poly (methyl methacrylate).

10. The method of claim 1, further comprising:
(a) injecting a dental reline material in one or more gaps defined between gum tissue of the alveolar arch and a corresponding surface of the dental prosthetic; and
(b) modifying a configuration of the dental prosthetic based on the injected dental reline material.

11. The method of claim 1, further comprising:
(a) injecting a dental impression material in one or more gaps defined between gum tissue of the alveolar arch and a corresponding surface of the dental prosthetic; and
(b) modifying a configuration of the dental prosthetic based on the injected dental impression material.

12. The method of claim 1, wherein utilizing the first guide member to achieve a substantially planar bone surface along the alveolar arch comprises one or both of removing bone protruding past a plane defined by a horizontal surface of the first guide member or adding bone augmentation material to bone recessed below a plane defined by a horizontal surface of the first guide member.

13. A method of installing a dental prosthetic device, the method comprising:
(a) securing a first guide member to an alveolar arch in a mouth of a patient;
(b) utilizing the first guide member to achieve a substantially planar bone surface along the alveolar arch;
(c) coupling a second guide member with the first guide member;
(d) utilizing the second guide member to install one or more implants in the alveolar arch through substantially planar bone surface;
(e) securing one or more abutments to the one or more implants;
(f) securing one or more metallic inserts to the one or more abutments via one or more inserted screws, the one or more inserted screws being inserted through a dental prosthetic, wherein the dental prosthetic comprises a nanoceramic material;
(g) applying cement in one or more recesses formed in the dental prosthetic;
(h) positioning the dental prosthetic on the one or more metallic inserts such that the one or more metallic inserts are received in the one or more recesses formed in the dental prosthetic;
(i) waiting for the cement to cure such that the one or more metallic inserts are secured to the dental prosthetic via the cement;
(j) removing the one or more metallic inserts and the dental prosthetic from the one or more abutments, wherein the one or more metallic inserts remain secured to the dental prosthetic via the cement after removing the one or more metallic inserts and the dental prosthetic from the one or more abutments; and
(k) securing the dental prosthetic to the one or more implants via the one or more metallic inserts and the one or more abutments.

14. A method of installing a dental prosthetic device, the method comprising:
(a) securing a first guide member to an alveolar arch in a mouth of a patient;
(b) utilizing the first guide member to achieve a substantially planar bone surface along the alveolar arch;
(c) coupling a second guide member with the first guide member;
(d) utilizing the second guide member to install one or more implants in the alveolar arch through substantially planar bone surface;
(e) securing a dental prosthetic to the one or more implants, wherein the dental prosthetic comprises a nanoceramic material;
(f) injecting a dental reline material or a dental impression material in one or more gaps defined between gum tissue of the alveolar arch and a corresponding surface of the dental prosthetic; and
(g) modifying a configuration of the dental prosthetic based on the injected dental reline material or dental impression material.

* * * * *